US012472290B2

(12) United States Patent
Homma et al.

(10) Patent No.: US 12,472,290 B2
(45) Date of Patent: Nov. 18, 2025

(54) BLOOD PURIFICATION APPARATUS

(71) Applicant: Nikkiso Co., Ltd., Tokyo (JP)

(72) Inventors: Takumi Homma, Shizuoka (JP); Kazuya Tsuji, Shizuoka (JP); Hikaru Chiaki, Shizuoka (JP); Yuya Menjoh, Shizuoka (JP); Kunihiko Akita, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 327 days.

(21) Appl. No.: 18/014,772

(22) PCT Filed: Jun. 7, 2021

(86) PCT No.: PCT/JP2021/021637
§ 371 (c)(1),
(2) Date: Jan. 6, 2023

(87) PCT Pub. No.: WO2022/009584
PCT Pub. Date: Jan. 13, 2022

(65) Prior Publication Data

US 2024/0238491 A1 Jul. 18, 2024

(30) Foreign Application Priority Data

Jul. 9, 2020 (JP) ................................ 2020-118794

(51) Int. Cl.
*A61M 1/16* (2006.01)

(52) U.S. Cl.
CPC ................................ *A61M 1/1603* (2014.02)

(58) Field of Classification Search
CPC ........... A61M 1/3643; A61M 1/36225; A61M 1/3434; A61M 39/10
See application file for complete search history.

(56) References Cited

FOREIGN PATENT DOCUMENTS

| | | | |
|---|---|---|---|
| JP | 2012-34782 | A | 2/2012 |
| JP | 5693890 | B2 | 4/2015 |
| JP | 2018-139791 | A | 9/2018 |

OTHER PUBLICATIONS

International Preliminary Report on Patentability for Application No. PCT/JP2021/021637, form IB338, dated Jan. 19, 2023, 7 pgs.
International Preliminary Report on Patentability for Application No. PCT/JP2021/021637, form IB326, dated Jan. 19, 2023, 7 pgs.

*Primary Examiner* — Leslie R Deak
(74) *Attorney, Agent, or Firm* — Young Basile Hanlon & MacFarlane, P.C.

(57) ABSTRACT

Provided is a blood purification apparatus that returns blood in a blood circuit to a body. A blood purification apparatus includes: a blood circuit and a dialysate circuit coupled to each other through a blood purifier; an air introduction route coupled to the dialysate circuit; an air introducer provided to any of the dialysate circuit and the air introduction route and configured to set the dialysate circuit to a positive pressure by introducing air into the dialysate circuit through the air introduction route; and a controller configured to control the air introducer in such a way as to feed a dialysate from the dialysate circuit to the blood circuit, and to control the blood circuit and the dialysate circuit in such a way as to return blood in the blood circuit and the blood purifier to a body by feeding the dialysate from the dialysate circuit to the blood circuit.

13 Claims, 11 Drawing Sheets

BLOOD PURIFICATION APPARATUS

CROSS-REFERENCE TO RELATED APPLICATION(S)

This application is a national stage application of International Application No. PCT/JP2021/021637, filed on Jun. 7, 2021, which claims priority to Japanese Application No. 2020-118794, filed on Jul. 9, 2020, the entire disclosures of which are hereby incorporated by reference.

TECHNICAL FIELD

The present disclosure relates to a blood purification apparatus, or more specifically, to a blood purification apparatus that returns blood remaining in a blood circuit to a body by using a dialysate in a dialysate filter.

BACKGROUND ART

In a case where kidneys that constitute part of organs of a human do not operate normally (a renal failure), functions to produce urine out of extra water in the body, to excrete unwanted waste products in the body, and so forth do not work well. To deal with the renal failure, a blood purification apparatus (a dialysis apparatus) is used for conducting a therapy (a dialysis treatment) to extracorporeally circulate blood from a patient and to filter waste products and water in the blood by using a blood purifier.

The blood purification apparatus withdraws blood from a patient and introduces the blood into the blood purifier (a blood flow route) through a blood circuit while introducing a dialysate from a supply source of the dialysate (a dialysate supplier) into the blood purifier (a dialysate flow route) through a dialysate circuit at the same time. The blood purification apparatus purifies the blood by exchanging components such as waste products and electrolytes between the blood and the dialysate through the blood purifier, and returns the purified blood to the body. Since the blood remains in the blood circuit after the introduction of the blood into the blood circuit in the dialysis treatment, an operation to return the remaining blood to the body (blood return) is generally carried out by feeding normal saline into the blood circuit. The dialysate may also be used as a substitute liquid for this normal saline.

CITATION LIST

Patent Literature

PTL 1: Japanese Patent No. 5693890

SUMMARY OF INVENTION

PTL 1 discloses a blood purification apparatus configured to return blood in a blood circuit to a body by supplying a dialysate in a filter to the blood circuit. The blood purification apparatus described in PTL 1 introduces air into the filter through an air introduction line, and draws the dialysate in the filter into the blood circuit by rotating a blood pump that is operated by a backup battery. This configuration enables blood return even in a case where power supply to the blood purification apparatus is stopped.

The blood purification apparatus described in PTL 1 releases the air at a tip of the air introduction line and rotates the blood pump in order to draw out the dialysate in the blood circuit. Accordingly, a circuit portion at an entrance side of the blood pump is prone to be set to a negative pressure due to a pressure generated by rotation of the blood pump. This is not desirable in light of conducting the blood return.

The present invention provides a blood purification apparatus that returns blood to a patient while preventing or relaxing a negative pressure inside a blood circuit.

A blood purification apparatus of an embodiment includes: a blood circuit and a dialysate circuit coupled to each other through a blood purifier; an air introduction route coupled to the dialysate circuit; an air introducer provided to any of the dialysate circuit and the air introduction route and configured to set the dialysate circuit to a positive pressure by introducing air into the dialysate circuit through the air introduction route; and a controller configured to control the air introducer in such a way as to feed a dialysate from the dialysate circuit to the blood circuit, and to control the blood circuit and the dialysate circuit in such a way as to return blood in the blood circuit and the blood purifier to a body by feeding the dialysate from the dialysate circuit to the blood circuit.

A method to be executed by a blood purification apparatus of another embodiment is a method to be executed by a blood purification apparatus provided with a blood circuit and a dialysate circuit coupled to each other through a blood purifier, an air introduction route coupled to the dialysate circuit, an air introducer provided to any of the dialysate circuit and the air introduction route and configured to set the dialysate circuit to a positive pressure by introducing air into the dialysate circuit through the air introduction route, and a controller, the method comprising the steps of: causing the controller to control the air introducer in such a way as to feed a dialysate from the dialysate circuit to the blood circuit; and causing the controller to control the blood circuit and the dialysate circuit in such a way as to return blood in the blood circuit and the blood purifier to a body by feeding the dialysate from the dialysate circuit to the blood circuit.

According to the blood purification apparatus of the embodiment, it is possible to prevent the blood circuit from being set to a negative pressure or relaxing a state of the negative pressure.

DESCRIPTION OF EMBODIMENTS

Blood purification apparatuses (dialysis apparatuses) according to embodiments will be described below with reference to the accompanying drawings. A blood purification apparatus according to each embodiment returns blood that remains in a blood circuit to a body (blood return) by using a dialysate in a dialysate filter in a case where power supply from a main power source to the blood purification apparatus is stopped due to blackout and the like, for example. In order to carry out this blood return, some constituents of the blood purification apparatus are operated by power supply from a backup power source.

First Embodiment

Figure 1:
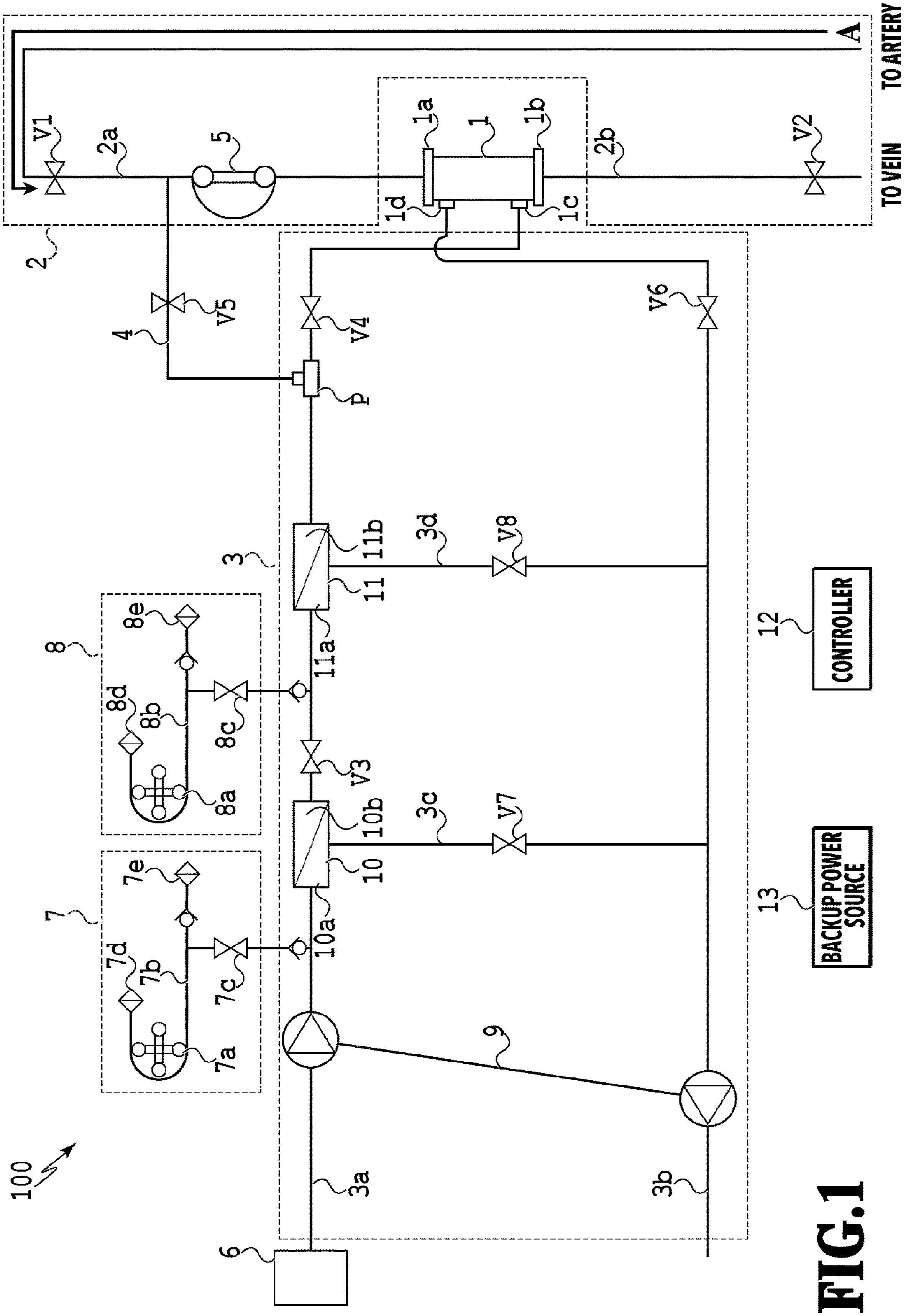
FIG. 1 is an overall configuration diagram of a blood purification apparatus according to a first embodiment.

FIG. 1 is a block diagram showing a configuration of a blood purification apparatus 100 according to a first embodiment. The blood purification apparatus 100 includes a blood purifier 1, a blood circuit 2, a dialysate circuit 3, a rehydration circuit 4, a blood pump 5, a dialysate supplier 6, a primary air introducer 7, a secondary air introducer 8, a dual pump 9, a dialysate filter 10, a dialysate filter 11, a controller 12, and a backup power source 13 as main constituents. The constituents shown in FIG. 1 merely represent examples of constituents for implementing the present embodiment, and a chamber for trapping bubbles of the blood flowing in the blood circuit 2, a water removal line and a water removal pump for removing water from the blood of a patient, and the like are also provided in reality.

The blood purifier 1, which is also referred to as a dialyzer, purifies blood of a patient. The blood purifier 1 includes a blood introduction inlet 1*a* that introduces the blood from the blood circuit 2, and a blood introduction outlet 1*b* that discharges the purified blood. Moreover, the blood purifier 1 includes a dialysate introduction inlet 1*c* that introduces a dialysate from the dialysate circuit 3, and a dialysate drainage outlet 1*d* that drains the dialysate (drainage). Furthermore, the blood purifier 1 includes a blood purification membrane that is provided inside. The blood purification membrane is formed from a bundle of hollow fibers having pores on side surfaces (a hollow fiber membrane). An inner side of the blood purification membrane is a blood flow route (not shown) and an outer side of the blood purification membrane (the hollow fibers) is a dialysate flow route (not shown).

The blood to flow in the blood purifier 1 flows in the blood flow route and unwanted substances such as uremic substances are removed by passing through the pores in the blood purification membrane by one or both of diffusion and ultrafiltration. The dialysate to flow in the blood purifier 1 flows in the dialysate flow route and the blood is supplemented only with substances such as electrolytes included in the dialysate, which are necessary for a human body. Here, the inner side of the blood purification membrane can also function as the dialysate flow route and the outer side of the blood purification membrane can also function as the blood flow route.

The blood circuit 2 and the dialysate circuit 3 are coupled to each other through the blood purification membrane of the blood purifier 1, and are configured to bidirectionally circulate the blood and the dialysate. The blood circuit 2 is a flow route that introduces the blood removed from the patient into the blood purifier 1 and returns the blood discharged from the blood purifier 1 (the purified blood) to the body (the blood flows in a direction indicated with an arrow A in FIG. 1) at the time of a dialysis treatment. The blood circuit 2 is mainly formed from a tube that enables passage of the blood. The blood circuit 2 includes a blood removal side circuit 2*a* and a blood return side circuit 2*b*.

The blood removal side circuit 2*a* is a flow route that introduces the blood removed from the patient into the blood purifier 1. One end of the blood removal side circuit 2*a* is attached to a blood removal side puncture needle (not shown) that is punctured into a blood vessel of the patient, and another end thereof is joined to the blood introduction inlet 1*a*. An on-off valve (a solenoid valve) V1 is provided to the blood removal side circuit 2*a*. A flow of the blood in the blood removal side circuit 2*a* is controlled by opening and closing the on-off valve V1. The blood return side circuit 2*b* is a flow route that returns the blood discharged from the blood purifier 1 to the body. One end of the blood return side circuit 2*b* is attached to a blood return side puncture needle (not shown) that is punctured into a blood vessel of the patient, and another end thereof is joined to the blood introduction outlet 1*b*. An on-off valve (a solenoid valve) V2 is provided to the blood return side circuit 2*b*. A flow of the blood in the blood return side circuit is controlled by opening and closing the on-off valve V2.

The blood pump 5 is provided to the blood removal side circuit 2*a* and configured to deliver a liquid in the blood circuit 2 in a direction of movement from the blood removal side circuit 2*a* to the blood return side circuit 2*b* (hereinafter referred to as a normal direction in delivering liquid) or in a direction of movement from the blood return side circuit 2*b* to the blood removal side circuit 2*a* (hereinafter referred to as a reverse direction in delivering liquid). The blood pump 5 is formed from a peristaltic pump that includes a stator and a rotor, and the peristaltic pump is driven in such a way as to rotate the rotor. The rotor is rotated by an actuator (not shown) such as an electric motor under control of the controller 12. The blood pump 5 is provided with a rotary encoder (not shown). The rotary encoder detects the number of rotations of the rotor. By forward rotation of the blood pump 5, the blood removal side circuit 2*a* pinched between the stator and the rotor is squeezed so as to generate the flow in the normal direction in delivering liquid. Meanwhile, by reverse rotation of the blood pump 5, the blood removal side circuit 2*a* is squeezed so as to generate the flow in the reverse direction in delivering liquid.

The dialysate circuit 3 is a flow route that supplies the dialysate to the blood purifier 1 and/or the blood circuit 2, and discharges the drainage of the dialysate from the blood purifier 1. The dialysate circuit 3 is mainly formed from a tube that enables passage of the dialysate. The dialysate circuit 3 includes a dialysate introduction circuit 3*a*, a dialysate drainage circuit 3*b*, a dialysate bypass circuit 3*c*, and a dialysate bypass circuit 3*d*.

The dialysate introduction circuit 3*a* is a flow route from the dialysate supplier 6 to the dialysate introduction inlet 1*c*. The dialysate flows in the blood purifier 1 by way of the dialysate introduction circuit 3*a*. An on-off valve (a solenoid valve) V3, an on-off valve (a solenoid valve) V4, and a dialysate port P are provided to the dialysate introduction circuit 3*a*. A flow of the dialysate into the blood purifier 1 is controlled by opening and closing the on-off valve V3 and the on-off valve V4. The dialysate port P takes out the dialysate.

The dialysate drainage circuit 3*b* is a flow route from the dialysate drainage outlet 1*d* to a dialysate drainer (not shown). The drainage from the blood purifier 1 is drained to the dialysate drainer by way of the dialysate drainage circuit 3*b*. An on-off valve (a solenoid valve) V6 is provided to the dialysate drainage circuit 3*b*. A flow of the drainage to the dialysate drainer is controlled by opening and closing the on-off valve V6.

Each of the dialysate bypass circuit 3*c* and the dialysate bypass circuit 3*d* is a flow route from the dialysate introduction circuit 3*a* to the dialysate drainage circuit 3*b*. An on-off valve (a solenoid valve) V7 is provided to the dialysate bypass circuit 3*c*. Likewise, an on-off valve (a solenoid valve) V8 is provided to the dialysate bypass circuit 3*d*. A flow of the dialysate from the dialysate introduction circuit 3*a* to the dialysate drainage circuit 3*b* is controlled by opening and closing the on-off valves V7 and V8.

The dialysate bypass circuit 3*c* and the dialysate bypass circuit 3*d* are the flow routes for preventing the inappropriate dialysate from flowing into the blood circuit 2. For example, the blood purification apparatus 100 is provided with a warmer (not shown) for warming the dialysate. In the case where the temperature of the dialysate exceeds a predetermined temperature due to the warmer at the time of the dialysis treatment, the dialysate flows to the dialysate drainage circuit 3*b* through the dialysate bypass circuit 3*c* and/or the dialysate bypass circuit 3*d* in order to prevent the dialysate at the high temperature from flowing to the blood circuit 2. In this case, the on-off valve V7 and/or the on-off valve V8 are opened.

The rehydration circuit 4 is a connection flow route that connects the blood circuit 2 to the dialysate circuit 3 while bypassing the blood purifier 1. Specifically, the rehydration circuit 4 is a flow route from the dialysate port P to the blood removal side circuit 2*a* for supplying the dialysate from the dialysate circuit 3 to the blood circuit 2 while bypassing the blood purifier 1. An on-off valve (a solenoid valve) V5 is provided to the rehydration circuit 4. A flow of the dialysate to the blood removal side circuit 2*a* is controlled by opening and closing the on-off valve V5.

The dialysate supplier 6 introduces the dialysate into the dialysate introduction circuit 3*a*. Here, the dialysate supplier 6 receives supply of pure water from a not-illustrated pure water machine (an RO water machine) provided outside the blood purification apparatus 100, and receives supply of (suctions) an undiluted solution from a not-illustrated undiluted solution tank externally mounted on the blood purification apparatus 100. Subsequently, the dialysate supplier 6 produces the dialysate by mixing the undiluted solution of the dialysate with the pure water in a predetermined proportion, and introduces the dialysate into the dialysate introduction circuit 3*a*. In this embodiment, the blood purification apparatus 100 includes the dialysate supplier 6. However, without limitation to the foregoing, the dialysate supplier 6 may be externally provided as a dialysate supply apparatus, and the blood purification apparatus may receive the supply of the dialysate from the dialysate supply apparatus.

While the dialysate supplier 6 generates the dialysate and introduces the dialysate into the dialysate introduction circuit 3*a* at normal times (such as at the time of the dialysis treatment), generation of the new dialysate may be restricted in the event of a blackout and the like. In this case, the supply of the dialysate from the dialysate supplier 6 to the dialysate circuit 3 is stopped and the dialysate stored in the dialysate filter 10 and/or the dialysate filter 11 is introduced into the dialysate circuit 3 instead. Details will be described later.

The primary air introducer 7 introduces the air into the (primary) dialysate filter 10 to be described later. The air is introduced into the dialysate filter 10 by the primary air introducer 7. In the case where the air is introduced into the dialysate filter 10, the dialysate filter 10 is set to a positive pressure and the dialysate stored in the dialysate filter 10 flows to the dialysate circuit 3 (the dialysate port P). In other words, the primary air introducer 7 plays roles in pushing the dialysate stored in the dialysate filter 10 out to the dialysate circuit 3, and feeding the dialysate to the dialysate circuit 3 (the dialysate introduction circuit 3*a*) and the blood circuit 2.

The primary air introducer 7 includes an air pump 7*a*, an air introduction route 7*b*, an on-off valve (a solenoid valve) 7*c*, an air filter 7*d*, and an air filter 7*e*. The air pump 7*a* incorporates a rotor and drives the rotor so as to perform rotation. The rotor is rotated by an actuator (not shown) such as an electric motor under control of the controller 12. The air pump 7*a* is provided with a rotary encoder (not shown). The rotary encoder detects the number of rotations of the rotor. By the rotation of the air pump 7*a*, the air is introduced into the dialysate filter 10 through the air introduction route 7*b*.

The air introduced into the dialysate filter 10 by the drive of the air pump 7*a* generates a flow of the dialysate to the dialysate circuit 3 (the dialysate introduction circuit 3*a*) and the blood circuit 2. The flow of the air to the dialysate filter 10 is controlled by opening and closing the on-off valve 7*c* provided between the air pump 7*a* and the dialysate filter 10. The air filter 7*d* and the air filter 7*e* remove dust in the air.

The secondary air introducer 8 introduces the air into the (secondary) dialysate filter 11 to be described later. The air is introduced into the dialysate filter 11 by the secondary air introducer 8. In the case where the air is introduced into the dialysate filter 11, the dialysate filter 11 is set to a positive pressure and the dialysate stored in the dialysate filter 11 flows to the dialysate circuit 3 (the dialysate port P). In other words, the secondary air introducer 8 plays roles in pushing the dialysate stored in the dialysate filter 11 out to the dialysate circuit 3, and in feeding the dialysate to the dialysate circuit 3 (the dialysate introduction circuit 3*a*) and the blood circuit 2.

The secondary air introducer 8 includes an air pump 8*a*, an air introduction route 8*b*, an on-off valve (a solenoid valve) 8*c*, an air filter 8*d*, and an air filter 8*e*. The air pump 8*a* incorporates a rotor and drives the rotor so as to perform rotation. The rotor is rotated by an actuator (not shown) such as an electric motor under control of the controller 12. The air pump 8*a* is provided with a rotary encoder (not shown). The rotary encoder detects the number of rotations of the rotor. By the rotation of the air pump 8*a*, the air is introduced into the dialysate filter 11 through the air introduction route 8*b*.

The air introduced into the dialysate filter 11 by the drive of the air pump 8*a* generates a flow of the dialysate to the dialysate circuit 3 (the dialysate introduction circuit 3*a*) and the blood circuit 2. The flow of the air to the dialysate filter 11 is controlled by opening and closing the on-off valve 8*c* provided between the air pump 8*a* and the dialysate filter 11. The air filter 8*d* and the air filter 8*e* remove dust in the air.

One or both of the primary air introducer 7 (the air pump 7*a*) and the secondary air introducer 8 (the air pump 8*a*) play a role in adjusting liquid levels of the liquid in chambers provided to the blood circuit 2 at the time of the dialysis treatment, for example. This liquid level adjustment will be described later.

Note that the on-off valve 7*c*, the air filter 7*d*, and the air filter 7*e* are not essential structures in the primary air introducer 7. Likewise, the on-off valve 8*c*, the air filter 8*d*, and the air filter 8*e* are not essential structures in the secondary air introducer 8.

The dual pump 9 is provided across the dialysate introduction circuit 3*a* and the dialysate drainage circuit 3*b*. The dual pump 9 introduces the dialysate to a downstream side in a liquid delivery direction of the dialysate introduction circuit 3*a*, and meanwhile, discharges the drainage of the dialysate to a downstream side in the liquid delivery direction of the dialysate drainage circuit 3*b*. In other words, the dual pump 9 plays roles as a dialysate supply pump for supplying the dialysate to the blood circuit 2 and as a dialysate drainage pump for draining the dialysate from the dialysate drainer. Here, a plunger (not shown) is provided inside a housing of the dual pump 9. A volume on the dialysate introduction circuit 3*a* side and a volume on the dialysate drainage circuit 3*b* side are defined while interposing the plunger in between, and the introduction of the dialysate and the discharge of the drainage are interlocked with reciprocation of the plunger.

The dialysate filter 10 purifies the dialysate by trapping substances such as endotoxins contained in the dialysate supplied from the dialysate supplier 6. The dialysate filter 10 is provided to the dialysate circuit 3, and includes a primary chamber 10*a* and a secondary chamber 10*b*. Meanwhile, a dialysate purification membrane is provided inside the dialysate filter 10. The dialysate purification membrane is formed from a bundle of hollow fibers (a hollow fiber membrane) with side walls provided with pores. The dialysate filter 10 is configured such that the dialysate flows from the primary chamber 10*a* (an inner side of the dialysate purification membrane) to the secondary chamber 10*b* (an outer side of the dialysate purification membrane). The dialysate filter 10 has a property of blocking passage of the air with surface tension of water molecules by passing water thereto.

The primary chamber 10*a* and the secondary chamber 10*b* can store the dialysate supplied from the dialysate supplier 6. In other words, at the time of the dialysis treatment, the dialysate to be purified is stored in the primary chamber 10*a* while the purified dialysate is stored in the secondary chamber 10*b*. The stored dialysate is supplied to the dialysate circuit 3 by the primary air introducer 7 as described later. Here, the primary chamber 10*a* may be located on the outer side of the dialysate purification membrane and the secondary chamber 10*b* may be located on the inner side of the dialysate purification membrane.

The dialysate filter 11 purifies the dialysate by trapping the substances such as endotoxins contained in the dialysate supplied from the dialysate supplier 6. The dialysate filter 11 is provided to the dialysate circuit 3, and includes a primary chamber 11*a* and a secondary chamber 11*b*. Meanwhile, a dialysate purification membrane is provided inside the dialysate filter 11. The dialysate purification membrane is formed from a bundle of hollow fibers (a hollow fiber membrane) with side walls provided with pores. The dialysate filter 11 is configured such that the dialysate flows from the primary chamber 11*a* (an inner side of the dialysate purification membrane) to the secondary chamber 11*b* (an outer side of the dialysate purification membrane). The dialysate filter 11 has a property of blocking passage of the air with surface tension of water molecules by passing water thereto.

The primary chamber 11*a* and the secondary chamber 11*b* can store the dialysate supplied from the dialysate supplier 6. In other words, at the time of the dialysis treatment, the dialysate to be purified is stored in the primary chamber 11*a* while the purified dialysate is stored in the secondary chamber 11*b*. The stored dialysate is supplied to the dialysate circuit 3 by the secondary air introducer 8 as described later. Here, the primary chamber 11*a* may be located on the outer side of the dialysate purification membrane and the secondary chamber 11*b* may be located on the inner side of the dialysate purification membrane.

The filters such as the dialysate filter 10 and the dialysate filter 11 are generally provided to the blood purification apparatus in order to remove impurities contained in the dialysate at the time of the dialysis treatment. In the present embodiment, the pair of the dialysate filter 10 and the dialysate filter 11 are provided to the dialysate circuit 3, so that the dialysate can be purified even in the case where one of the filters fails to function.

The controller 12 is a processing device that controls the entire blood purification apparatus 100 including the air pump 7*a* and the air pump 8*a* mentioned above, and so forth. The controller 12 includes an arithmetic device and a storage device (a storage device such as a RAM and a ROM). The arithmetic device may be implemented by a processor such as a CPU and a microcontroller, an ASIC (application specific integrated circuit), an FPGA (field programmable gate array), and the like, but its mode is not limited.

The backup power source 13 is a power unit that supplies electric power to some of the constituents such as the controller 12 in the case where power supply from the main power source (not shown) to the blood purification apparatus 100 is stopped due to blackout and the like, for example. By using the backup power source 13, as described later, the controller 12, the primary air introducer 7, the secondary air introducer 8, and the like function so that the blood remaining in the blood circuit 2 can be returned to the body.

In the above-described blood purification apparatus 100, the dialysate from the dialysate supplier 6 is introduced into the dialysate introduction circuit 3*a* by operating the dual pump 9 at the time of the dialysis treatment, and the dialysate is passed from the dialysate circuit 3 to the rehydration circuit 4, thus flowing in the blood purifier 1. Next, the dialysate is passed from the blood purifier 1 to the dialysate drainage circuit 3*b*, and is discharged from the dialysate drainer. Meanwhile, at the time of the dialysis treatment, the blood flows in the normal direction in delivering liquid by the forward rotation of the blood pump 5. Due to the flow of the dialysate at the time of the dialysis treatment mentioned above, the purified dialysate is stored in the dialysate filter 10 and the dialysate filter 11.

Figure 2:
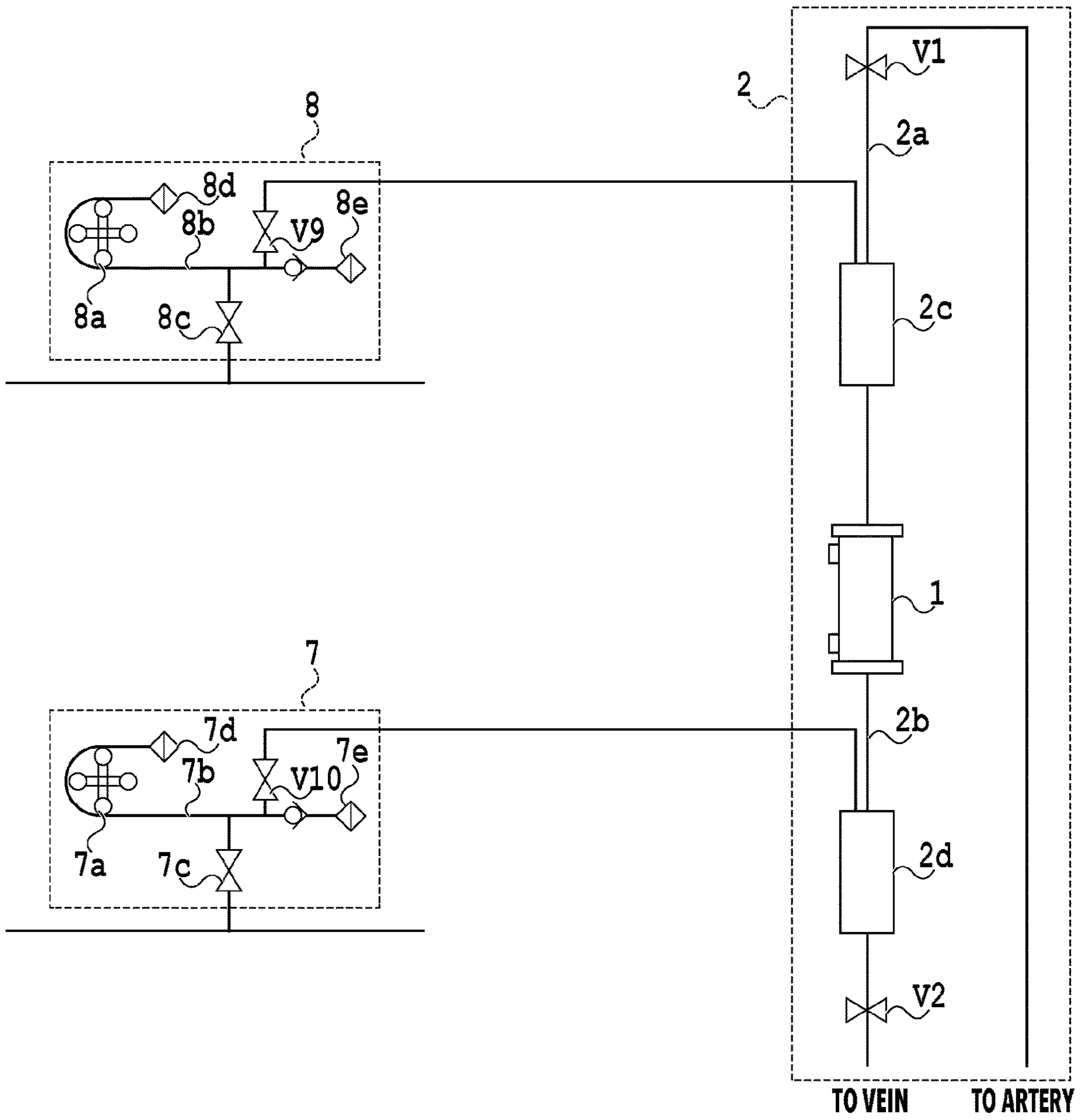
FIG. 2 is a diagram showing relations among air introducers and chambers in a blood circuit.

Next, relations among the primary air introducer 7, the secondary air introducer 8, and the chambers provided to the blood circuit 2 will be described with reference to FIG. 2. As mentioned above, one or both of the primary air introducer 7 and the secondary air introducer 8 play the role in adjusting the liquid levels of the liquid in the chambers provided to the blood circuit 2 at the time of the dialysis treatment, for example. In other words, the air pump 7*a* and/or the air pump 8*a* also play roles as liquid level adjustment pumps (the liquid level adjustment pumps are not usually used for the blood return). FIG. 2 shows a state where the air pump 7*a* and the air pump 8*a* function as the liquid level adjustment pumps. Here, instead of causing the air pump 7*a* and the air pump 8*a* to serve as the liquid level adjustment pumps, the air pump 7*a*, the air pump 8*a*, and the liquid level adjustment pump may be provided independently of one another.

In the blood circuit 2, a blood removal side air trap chamber 2*c* is provided to the blood removal side circuit 2*a*, and a blood return side air trap chamber 2*d* is provided to the blood return side circuit 2*b*. The blood removal side air trap chamber 2*c* is provided mainly for the purpose of trapping the air so as not to cause the air to flow into the blood purifier 1 and to develop air lock. The blood return side air trap chamber 2*d* is provided mainly for the purpose of trapping the air so as not to cause the air to flow into the body of the patient through the blood circuit 2. It is not always necessary to provide both of the blood removal side air trap chamber 2*c* and the blood return side air trap chamber 2*d*, and only one of them may be provided. In other words, the blood removal side air trap chamber 2*c* and the blood return side air trap chamber 2*d* play roles as chambers to contain the blood in the blood circuit 2.

The blood removal side air trap chamber 2*c* is coupled to the secondary air introducer 8 and an on-off valve (a solenoid valve) V9 is provided therebetween. The flow of the air from the secondary air introducer 8 to the blood removal side air trap chamber 2*c* is controlled by opening and closing the on-off valve V9 (the secondary air introducer 8 causes the air to flow to the blood removal side air trap chamber 2*c*). The blood return side air trap chamber 2*d* is coupled to the primary air introducer 7 and an on-off valve (a solenoid valve) V10 is provided therebetween. The flow of the air from the primary air introducer 7 to the blood return side air trap chamber 2*d* is controlled by opening and closing the on-off valve V10 (the primary air introducer 7 causes the air to flow to the blood return side air trap chamber 2*d*).

Each of the blood removal side air trap chamber 2*c* and the blood return side air trap chamber 2*d* includes two layers, namely, a blood layer and an air layer. The liquid level moves down as the air is accumulated in the chamber, which may lead to the occurrence of the air lock in which the air enters the hollow fibers in the blood purifier 1. In the example shown in FIG. 2, the primary air introducer 7 (the air pump 7*a*) rotates forward so as to introduce the air into the blood return side air trap chamber 2*d* and to move down the liquid level, or rotates in reverse so as to discharge the air from the blood return side air trap chamber 2*d* and to move up the liquid level. Likewise, the secondary air introducer 8 (the air pump 8*a*) rotates forward so as to introduce the air into the blood removal side air trap chamber 2*c* and to move down the liquid level, or rotates in reverse so as to discharge the air from the blood removal side air trap chamber 2*c* and to move up the liquid level.

FIG. 2 shows the example in which the blood removal side air trap chamber 2*c* is coupled to the secondary air introducer 8 and the blood return side air trap chamber 2*d* is coupled to the primary air introducer 7. However, this mode of connection is merely an example. For instance, the blood removal side air trap chamber 2*c* may be coupled to the primary air introducer 7 and the blood return side air trap chamber 2*d* may be coupled to the secondary air introducer 8. Alternatively, both of the blood removal side air trap chamber 2*c* and the blood return side air trap chamber 2*d* may be coupled to either the primary air introducer 7 or the secondary air introducer 8.

Next, processing according to the first embodiment will be described with reference to FIGS. 3 to 5. In the first embodiment, a description will be given of an example of returning the blood remaining in the blood purifier 1 and the blood circuit 2 to the body by using the dialysate in the dialysate filter 10 and the dialysate filter 11 (by sequentially introducing the air into the dialysate filter 10 and the dialysate filter 11) in the case where the power supply from the main power source to the blood purification apparatus 100 is stopped due to the blackout and the like, for instance. In the case where the power supply from the main power source to the blood purification apparatus 100 is stopped, only some of the constituents in the blood purification apparatus 100 to be described later function by the power supply from the backup power source 13. However, the dialysate supplier 6 stops the generation and supply of the dialysate. In this instance, the air pump 7*a* plays a role in feeding the dialysate in the dialysate filter 10 to the blood circuit 2 instead of adjusting the liquid level in the blood return side air trap chamber 2*d*. Likewise, the air pump 8*a* plays a role in feeding the dialysate in the dialysate filter 11 to the blood circuit 2 instead of adjusting the liquid level in the blood removal side air trap chamber 2*c*.

Meanwhile, the first embodiment adopts the blood return method of returning the blood to the body by introducing the dialysate from the dialysate circuit 3 to the blood circuit 2 through the blood purification membrane of the blood purifier 1 and causing the dialysate to push out the blood in the blood purifier 1 and the blood circuit 2. In the following, this blood return method will be referred to as a back filtration based blood return process. In the back filtration based blood return process, the dialysate flows in the dialysate circuit 3 and passes from the dialysate circuit 3 to the blood purifier 1. This flow of the dialysate causes the dialysate to pass through the dialysate flow route of the blood purifier 1, whereby the dialysate pushes out the blood through the pores in the blood purification membrane, thus returning the blood to the body.

Figure 3:
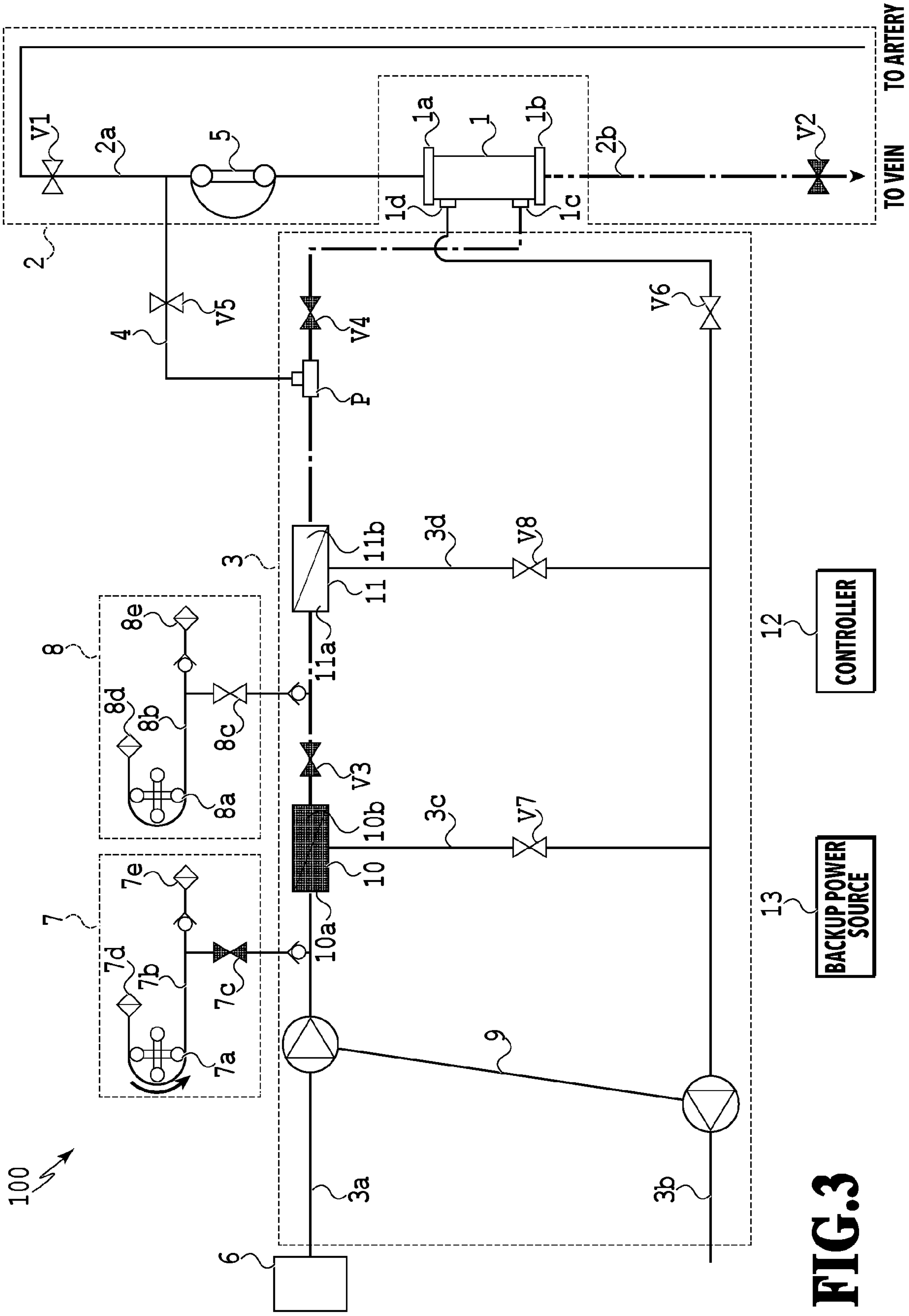
FIG. 3 is a diagram showing a flow of a dialysate in a back filtration based blood return process (a normal direction in delivering liquid) by using the dialysate in a (primary) dialysate filter.

FIG. 3 shows a flow of the dialysate in the case where the back filtration based blood return process is carried out by using the dialysate in the dialysate filter 10. In the example shown in FIG. 3, the blood is returned to the body in the normal direction in delivering liquid in the back filtration based blood return process. In the following drawings, valves among the valves (V1 to V6, V7*c*, and V8*c*) in the drawings are indicated with hatching in the case where the valves are opened, and the valves in the drawings are indicated with outlines in the case where the valves are closed.

As shown in FIG. 3, the on-off valve 7*c*, the on-off valve V3, the on-off valve V4, and the on-off valve V2 are opened in the back filtration based blood return process (the normal direction in delivering liquid). Meanwhile, the air pump 7*a* rotates forward. The opening of these on-off valves and the rotation of the air pump 7*a* are controlled by instructions of the controller 12. In particular, the controller 12 controls the number of rotations of the air pump 7*a* per unit time in such a way as to generate the flow of the dialysate to the dialysate circuit 3 (the dialysate introduction circuit 3*a*) and the blood circuit 2. In other words, the controller 12 controls a flow rate of the air from the primary air introducer 7. Although not illustrated, the on-off valve V10 shown in FIG. 2 is closed.

By driving the air pump 7*a* and opening the on-off valve 7*c*, the air is introduced into the dialysate filter 10 and the primary chamber 10*a* of the dialysate filter 10 is set to the positive pressure. Accordingly, the dialysate in the primary chamber 10*a* reaches the secondary chamber 10*b* and flows in the dialysate introduction circuit 3*a*. In other words, the controller 12 controls the dialysate circuit 3 and the blood circuit 2 such that the dialysate flows in the flow route shown in FIG. 3.

By opening the on-off valve V3, the on-off valve V4, and the on-off valve V2, the dialysate passes through the dialysate introduction circuit 3*a*, the blood purifier 1 (the blood purification membrane), and the blood return side circuit 2*b*. In FIG. 3, this flow of the dialysate is indicated with an arrow of a thick chain line. Here, the dialysate flows inside the blood purifier 1 in the order of the dialysate flow route, the blood purification membrane, and the blood flow route. By this flow of the dialysate, the dialysate pushes out the blood remaining in the blood purifier 1 and the blood circuit 2 (the blood return side circuit 2*b*), and the blood is returned to the body.

The back filtration based blood return process (the normal direction in delivering liquid) described with reference to FIG. 3 is carried out by operating at least the controller 12, the on-off valve 7*c*, the on-off valve V3, the on-off valve V4, the on-off valve V2, and the air pump 7*a* only by the power supply from the backup power source 13. On the other hand, the constituents such as the blood pump 5 and the dual pump 9 for feeding the dialysate to the dialysate circuit 3 and feeding the blood to the blood circuit 2 in the dialysis treatment may be stopped.

In the case where the dialysate in the dialysate filter 10 flows, the process is switched to the back filtration based blood return process (the normal direction in delivering liquid) using the dialysate in the dialysate filter 11. Specifically, in the back filtration based blood return process (the normal direction in delivering liquid), a supply source of the dialysate is switched from the dialysate filter 10 to the dialysate filter 11. This switching is carried out by the controller 12, and details thereof will be described later. FIG. 4 shows a flow of the dialysate in the case of carrying out the back filtration based blood return process (the normal direction in delivering liquid) by using the dialysate in the dialysate filter 11.

Figure 4:
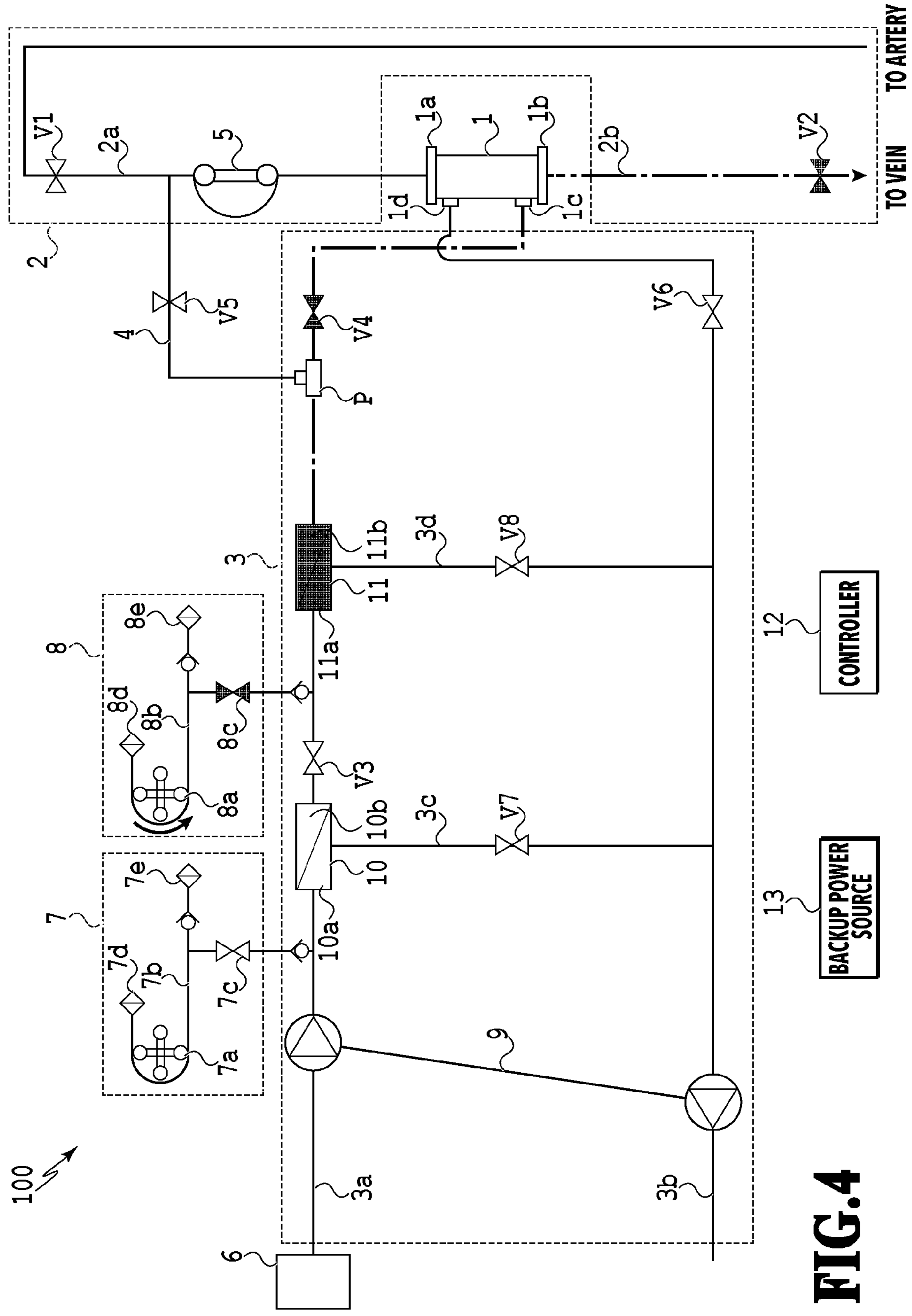
FIG. 4 is a diagram showing a flow of the dialysate in the back filtration based blood return process (the normal direction in delivering liquid) by using the dialysate in a (secondary) dialysate filter.

As shown in FIG. 4, in the case where the supply source of the dialysate is switched from the dialysate filter 10 to the dialysate filter 11, the on-off valve 7*c* is closed and the air pump 7*a* stops the rotation. Meanwhile, the air pump 8*a* rotates forward and the on-off valve 8*c* is opened. The opening and closing of these on-off valves, the stop of the rotation of the air pump 7*a*, and the rotation of the air pump 8*a* are controlled by instructions of the controller 12. In particular, the controller 12 controls the number of rotations of the air pump 8*a* per unit time in such a way as to generate the flow of the dialysate to the dialysate circuit 3 (the dialysate introduction circuit 3*a*) and the blood circuit 2. In other words, the controller 12 controls a flow rate of the air from the secondary air introducer 8. Although not illustrated, the on-off valve V9 shown in FIG. 2 is closed.

By driving the air pump 8*a* and opening the on-off valve 8*c*, the air is introduced into the dialysate filter 11 and the primary chamber 11*a* of the dialysate filter 11 is set to the positive pressure. Accordingly, the dialysate in the primary chamber 11*a* reaches the secondary chamber 11*b* and flows in the dialysate introduction circuit 3*a*. Thereafter, the dialysate flows in the same flow route as the flow route shown in FIG. 3. In other words, the controller 12 controls the dialysate circuit 3 and the blood circuit 2 such that the dialysate flows in the flow route shown in FIG. 4. In FIG. 4, this flow of the dialysate is indicated with an arrow of a thick chain line.

The back filtration based blood return process (the normal direction in delivering liquid) described with reference to FIG. 4 is carried out by operating at least the controller 12, the on-off valve 8*c*, the on-off valve V3, the on-off valve V4, the on-off valve V2, and the air pump 8*a* only by the power supply from the backup power source 13. On the other hand, the blood pump 5, the dual pump 9, and the like may be stopped.

In order to switch the supply source of the dialysate, the controller 12 determines that the dialysate in the dialysate filter 10 is introduced into (pushed out to) the dialysate circuit 3. This determination may be carried out by detecting that the primary chamber 10*a* is set to the positive pressure. In this case, a pressure gauge is provided to the primary chamber 10*a* and the pressure gauge detects a pressure of the air. The detected pressure value is transmitted to the controller 12. The controller 12 determines whether or not the pressure value exceeds a predetermined threshold.

Meanwhile, the determination may be carried out by detecting that bubbles are generated in the dialysate in the primary chamber 10*a*, because in the case where the air is introduced into the primary chamber 10*a*, the bubbles may be generated by the air that is mixed into the dialysate in the primary chamber 10*a*. In this case, an ultrasonic sensor is provided to the primary chamber 10*a*, for example, and the ultrasonic sensor detects a voltage corresponding to vibration of the dialysate. The bubbles have a higher attenuation rate than that of the dialysate. Accordingly, the generation of the bubbles can be detected by determining that the voltage value exceeds a predetermined threshold. The detected voltage value is transmitted to the controller 12. The controller 12 determines whether or not the voltage value exceeds a predetermined threshold.

Meanwhile, the determination may be carried out by measuring a temperature of the air introduced from the primary air introducer 7 and a temperature of a flow route (from the primary air introducer 7 to the dialysate filter 10) of the dialysate introduction circuit 3*a*, and determining whether or not the temperature of the dialysate introduction circuit 3*a* falls within a predetermined range based on the temperature of the introduced air. Because, in a case where a predetermined amount of the air is introduced to the dialysate filter 10, the temperature of the flow route comes close to the temperature of the introduced air. In this case, a thermometer is provided at an inlet of the primary air introducer 7, for example, and the thermometer measures the temperature of the air introduced from the primary air introducer 7. Meanwhile, another thermometer is also provided at the flow route between the primary air introducer 7 and the dialysate filter 10, and the thermometer detects the temperature of the flow route. Both of the detected temperature values are transmitted to the controller 12. The controller 12 determines whether or not each temperature value falls within a predetermined range.

Moreover, the determination may be carried out by determining whether or not the dialysate that flows in the dialysate introduction circuit 3*a* reaches a predetermined amount (such as a volume of the dialysate filter 10 (the primary chamber 10*a* and the secondary chamber 10*b*)). In this case, a flowmeter is provided to the dialysate introduction circuit 3*a* and the flowmeter measures a flow rate of the dialysate flowing in the dialysate introduction circuit 3*a*. The detected flow rate value is transmitted to the controller 12. The controller 12 determines whether or not the flow rate value reaches a predetermined amount.

In the present embodiment, the blood return is carried out by using the dialysate in the two dialysate filters (the dialysate filter 10 and the dialysate filter 11). For example, the supply source of the dialysate is switched from the dialysate filter 10 to the dialysate filter 11 in the case where it is not possible to return the blood sufficiently only with the dialysate in the dialysate filter 10. Here, the two dialysate filters (the dialysate filter 10 and the dialysate filter 11) are provided to the dialysate circuit 3 from a fail-safe point of view and are designed such that the amount of the dialysate that remains in the two dialysate filters corresponds to the amount of the blood that remains in the blood circuit 2. As a consequence, it is possible to carry out the blood return in a desired amount by introducing the air into the two dialysate filters. Here, the number of the dialysate filters is not limited only to two. For example, a single dialysate filter may be designed such that the amount of the dialysate remaining therein corresponds to the amount of the blood remaining in the blood circuit 2, and the blood return may be carried out likewise by introducing the air into the single dialysate filter only.

As described above, in the first embodiment, the back filtration based blood return process (the normal direction in delivering liquid) is carried out by using the dialysate in the dialysate filter 10 and the dialysate filter 11. According to the blood purification apparatus described in PTL 1, the introduction of the air into the filter through the air introduction line does not bring about the flow of the dialysate to the blood circuit, and the dialysate in the filter is drawn out to the blood circuit by driving the blood pump. Therefore, the blood purification apparatus described in PTL 1 has to drive the blood pump.

Meanwhile, according to the blood purification apparatus described in PTL 1, a portion of the circuit on the inlet side of the blood pump may be set to a negative pressure due to a pressure generated by the rotation of the blood pump for drawing out the dialysate in the blood circuit. The negative pressure in the blood circuit may cause burst of blood cell components (hemolysis) of the blood located inside and/or deterioration in ejection accuracy of the blood pump.

In the configuration of the first embodiment, the dialysate in the dialysate filter 10 flows to the dialysate circuit 3 and the blood circuit 2 by driving the air pump 7*a*. It is therefore not necessary to drive the blood pump 5 in order to draw out the dialysate. Moreover, in the configuration of the first embodiment, no pressure is generated in the blood circuit 2 for drawing out the dialysate, and the blood circuit 2 is hence not set to the negative pressure. The same applies to the case of using the dialysate in the dialysate filter 11. Therefore, according to the configuration of the first embodiment, it is possible to carry out the blood return more favorably as compared to the related art even in the case where the dialysate supplier 6 stops the generation and the supply of the dialysate.

Moreover, only the controller 12, the on-off valve 7*c*, the on-off valve V3, the on-off valve V4, the on-off valve V2, and the air pump 7*a* are operated in the configuration according to the first embodiment. From this perspective, it is possible to carry out the blood return by the power supply from the backup power source 13 to the minimum required constituents particularly in the case where the power supply from the main power source to the blood purification apparatus 100 is stopped.

Here, the blood pump 5 may be driven by also supplying the power from the backup power source 13 to the blood pump 5. In this case, the flows of the blood and the dialysate in the normal direction in delivering liquid are generated in the blood circuit 2. Accordingly, the blood pump 5 rotates forward. In other words, a pressure for drawing out the dialysate is generated in the blood circuit 2. In order not to set the blood circuit 2 to the negative pressure, the pressure in the dialysate circuit 3 caused by the introduction of the air into the dialysate filter 10 (or the dialysate filter 11) is controlled not to exceed a predetermined threshold. This threshold may be an experimentally obtained value for keeping the blood circuit 2 from being set to the negative pressure (or keeping the blood in the blood circuit 2 from being hemolyzed). Instead, the pressure in the dialysate circuit 3 generated by the introduction of the air into the dialysate filter 10 (or the dialysate filter 11) may be controlled such that the pressure becomes higher than (e.g., a higher pressure is achieved) a pressure in the blood circuit 2 generated by driving the blood pump 5.

The above-mentioned control may be carried out by performing control so as to rotate the air pump 7*a* and the blood pump 5 at predetermined numbers of rotations per unit time (to rotate the air pump 7*a* at a higher number of rotations per unit time than that of the blood pump 5, for example) such that the pressure in the dialysate circuit 3 does not exceed the threshold (or becomes higher than the pressure in the blood circuit 2), for example. The predetermined numbers of rotations may be experimentally obtained values. In this case, the encoders detect the number of rotations of the air pump 7*a* and the number of rotations of the blood pump 5. The detected numbers of rotations are transmitted to the controller 12. Based on the detected numbers of rotations, the controller 12 controls the air pump 7*a* and the blood pump 5 in such a way as to rotate the pumps at the predetermined numbers of rotations.

Likewise, the above-mentioned control may be carried out by performing control so as to rotate the air pump 8*a* and the blood pump 5 at predetermined numbers of rotations per unit time (to rotate the air pump 8*a* at a higher number of rotations per unit time than that of the blood pump 5, for example) such that the pressure in the dialysate circuit 3 does not exceed the threshold (or becomes higher than the pressure in the blood circuit 2), for example. In this case, the encoders detect the number of rotations of the air pump 8*a* and the number of rotations of the blood pump 5. The detected numbers of rotations are transmitted to the controller 12. Based on the detected numbers of rotations, the controller 12 controls the air pump 8*a* and the blood pump 5 in such a way as to rotate the pumps at the predetermined numbers of rotations.

Alternatively, the above-mentioned control may be carried out by controlling the number of rotations of the air pump 7*a* per unit time (or the number of rotations of the air pump 8*a* per unit time) and the number of rotations of the blood pump 5 per unit time based on the pressure in the dialysate circuit 3 and the pressure in the blood circuit 2. In this case, a pressure gauge is provided to the dialysate circuit 3 and the pressure gauge detects a pressure in the dialysate circuit 3. Meanwhile, another pressure gauge is provided to the blood circuit 2 and the pressure gauge detects a pressure in the blood circuit 2. The detected pressure values are transmitted to the controller 12, respectively. Based on the detected pressure values, the controller 12 controls both of them so as to increase the number of rotations of the air pump 7*a* per unit time (or the number of rotations of the air pump 8*a* per unit time), and/or to decrease the number of rotations of the blood pump 5 per unit time.

In the back filtration based blood return process, a back filtration based blood return process (the reverse direction in delivering liquid) to return the blood to the body in the reverse direction in delivering liquid may be carried out instead of or in addition to the blood return process described with reference to FIGS. 3 and 4. FIG. 5 shows a flow of the dialysate in the case of carrying out the back filtration based blood return process (the reverse direction in delivering liquid) by using the dialysate in the dialysate filter 10.

Figure 5:
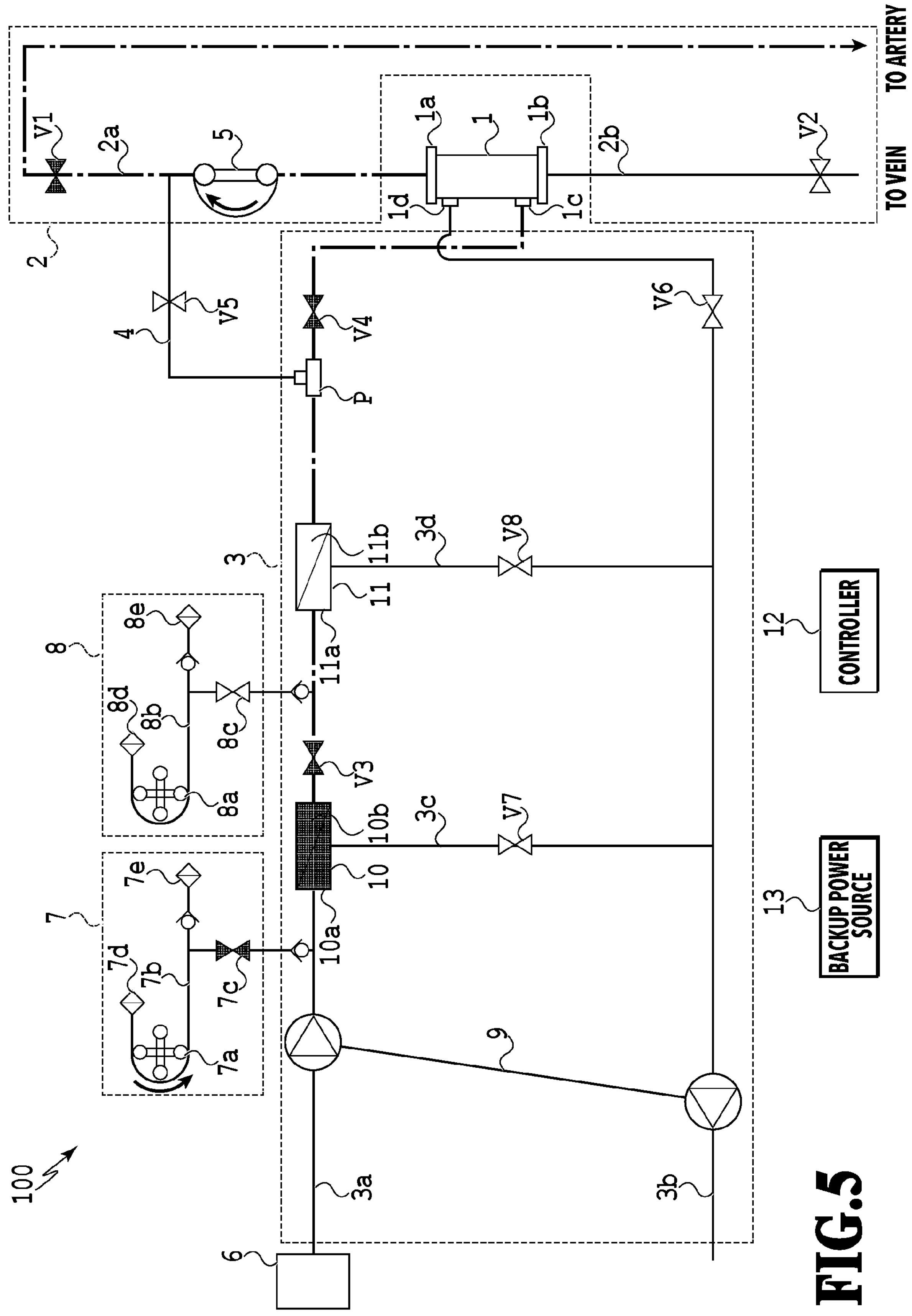
FIG. 5 is a diagram showing a flow of the dialysate in the back filtration based blood return process (a reverse direction in delivering liquid) by using the dialysate in the (primary) dialysate filter.

As shown in FIG. 5, the on-off valve 7*c*, the on-off valve V3, the on-off valve V4, and the on-off valve V1 are opened in the back filtration based blood return process (the reverse direction in delivering liquid). Meanwhile, the air pump 7*a* rotates forward. Moreover, the blood pump 5 rotates in reverse. The opening of these on-off valves, the rotation of the air pump 7*a*, and the rotation of the blood pump 5 are controlled by instructions of the controller 12. In particular, the controller 12 controls the number of rotations of the air pump 8*a* per unit time (controls the flow rate of the air in the secondary air introducer 8) in such a way as to generate the flow of the dialysate to the dialysate circuit 3 (the dialysate introduction circuit 3*a*) and the blood circuit 2.

By driving the air pump 7*a* and opening the on-off valve 7*c*, the air is introduced into the dialysate filter 10 and the primary chamber 10*a* of the dialysate filter 10 is set to the positive pressure. Accordingly, the dialysate in the primary chamber 10*a* reaches the secondary chamber 10*b* and flows in the dialysate introduction circuit 3*a*. In other words, the controller 12 controls the dialysate circuit 3 and the blood circuit 2 such that the dialysate flows in the flow route shown in FIG. 5.

By opening the on-off valve V3, the on-off valve V4, and the on-off valve V1, the dialysate passes through the dialysate introduction circuit 3*a*, the blood purifier 1 (the blood purification membrane), and the blood removal side circuit 2*a*. In FIG. 5, this flow of the dialysate is indicated with an arrow of a thick chain line. Here, the dialysate flows inside the blood purifier 1 in the order of the dialysate flow route, the blood purification membrane, and the blood flow route. By this flow of the dialysate, the dialysate pushes out the blood remaining in the blood purifier 1 and the blood circuit 2 (the blood removal side circuit 2*a*), and the blood is returned to the body.

The back filtration based blood return process (the reverse direction in delivering liquid) described with reference to FIG. 5 is carried out by operating at least the controller 12, the on-off valve 7*c*, the on-off valve V3, the on-off valve V4, the on-off valve V1, the air pump 7*a*, and the blood pump 5 only by the power supply from the backup power source 13. On the other hand, the constituents such as the dual pump 9 for feeding the dialysate to the dialysate circuit 3 in the dialysis treatment may be stopped.

In the case where the dialysate in the dialysate filter 10 flows, the supply source of the dialysate is switched from the dialysate filter 10 to the dialysate filter 11. The switching of the supply source of the dialysate has been described with reference to FIGS. 3 and 4, and detailed explanations thereof will be omitted. In the case where the supply source of the dialysate is switched from the dialysate filter 10 to the dialysate filter 11, the back filtration based blood return process (the reverse direction in delivering liquid) is carried out by using the dialysate in the dialysate filter 11.

The blood pump 5 is driven in the back filtration based blood return process (the reverse direction in delivering liquid). Accordingly, the air pump 7*a* (or the air pump 8*a*) and the blood pump 5 are controlled such that the pressure in the dialysate circuit 3 becomes higher than the pressure in the blood circuit 2. This control has been described with reference to FIGS. 3 and 4, and detailed explanations thereof will be omitted.

Here, both of the back filtration based blood return process (the normal direction in delivering liquid) and the back filtration based blood return process (the reverse direction in delivering liquid) may be carried out. For example, the back filtration based blood return process (the normal direction in delivering liquid) may be carried out in the first place by using the dialysate in the dialysate filter 10, and the back filtration based blood return process (the reverse direction in delivering liquid) may be carried out by using the dialysate in the dialysate filter 11 in the case of switching the supply source of the dialysate. Alternatively, the back filtration based blood return process (the reverse direction in delivering liquid) may be carried out in the first place by using the dialysate in the dialysate filter 10, and the back filtration based blood return process (the normal direction in delivering liquid) may be carried out by using the dialysate in the dialysate filter 11 in the case of switching the supply source of the dialysate. By carrying out both of the back filtration based blood return process (the normal direction in delivering liquid) and the back filtration based blood return process (the reverse direction in delivering liquid), it is possible to return the blood remaining in both of the blood removal side circuit 2*a* and the blood return side circuit 2*b* to the body.

Second Embodiment

Figure 6:
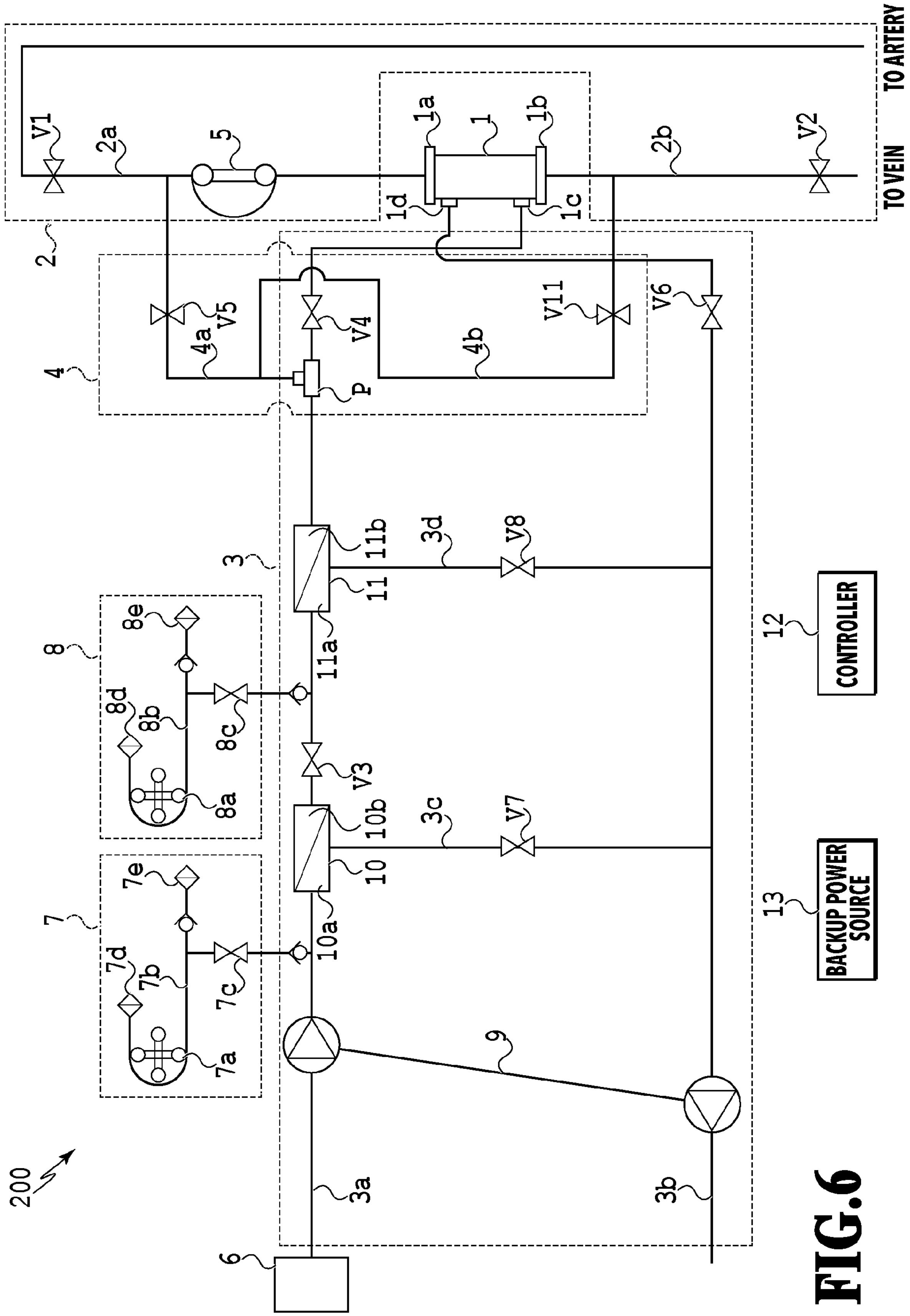
FIG. 6 is an overall configuration diagram of a blood purification apparatus according to a second embodiment.

FIG. 6 is a block diagram showing a configuration of a blood purification apparatus 200 according to a second embodiment. As compared to the blood purification apparatus 100 according to the first embodiment, the blood purification apparatus 200 has a different configuration of the rehydration circuit 4 and the configurations of the rest are the same. The rehydration circuit 4 of the blood purification apparatus 100 is the flow route from the dialysate port P to the blood removal side circuit 2*a*. Meanwhile, the rehydration circuit 4 of the blood purification apparatus 200 includes a blood removal side rehydration circuit 4*a* and a blood return side rehydration circuit 4*b*. The blood removal side rehydration circuit 4*a* corresponds to the rehydration circuit 4 of the blood purification apparatus 100.

The blood return side rehydration circuit 4*b* is a flow route from the dialysate port P to the blood return side circuit 2*b* for returning the blood in the blood circuit 2 to the body by a rehydration based blood return process (the reverse direction in delivering liquid) to be described later. An on-off valve (a solenoid valve) V11 is provided to the blood return side rehydration circuit 4*b*. The flow of the dialysate to the blood return side circuit 2*b* is controlled by opening and closing the on-off valve V11.

Next, processing according to the second embodiment will be described with reference to FIGS. 7 and 8. In the second embodiment, a description will be given only of an example of returning the blood remaining in the blood purifier 1 and the blood circuit 2 to the body by using the dialysate in the dialysate filter 10. However, the dialysate in the dialysate filter 11 may also be used in the second embodiment as with the first embodiment. Specifically, in the case where the dialysate in the dialysate filter 10 flows, the supply source of the dialysate is switched from the dialysate filter 10 to the dialysate filter 11. Only some of the constituents to be described later function by the power supply from the backup power source 13 in the blood purification apparatus 200 as well.

The second embodiment adopts the blood return method of returning the blood to the body by introducing the dialysate to the blood circuit 2 through the rehydration circuit 4 and causing the dialysate to push out the blood in the blood circuit 2. In the following, this blood return method will be referred to as the rehydration based blood return process. In the rehydration based blood return process, the dialysate flows in the dialysate circuit 3 and passes from the dialysate circuit 3 to the rehydration circuit 4 and the blood circuit 2. This flow of the dialysate causes the dialysate to flow in the blood circuit of the blood purifier 1, whereby the dialysate pushes out the blood remaining in the blood circuit 2 and the blood purifier 1, thus returning the blood to the body.

Figure 7:
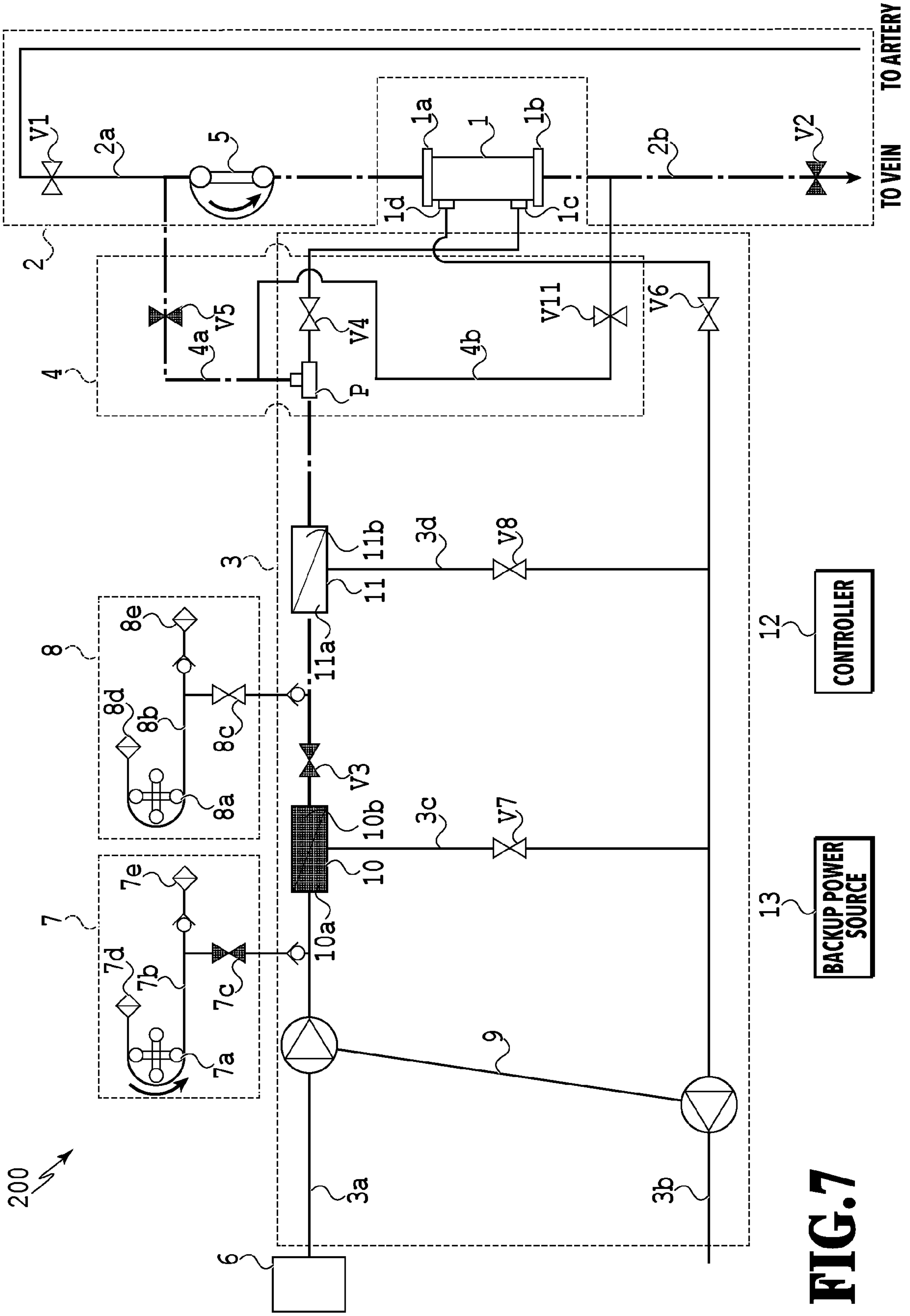
FIG. 7 is a diagram showing a flow of the dialysate in a rehydration based blood return process (the normal direction in delivering liquid) by using the dialysate in the (primary) dialysate filter.

FIG. 7 shows a flow of the dialysate in the case where the rehydration based blood return process is carried out by using the dialysate in the dialysate filter 10. In the example shown in FIG. 7, the blood is returned to the body in the normal direction in delivering liquid in the rehydration based blood return process. In the following drawings, valves among the valves in the drawings are indicated with hatching in the case where the valves are opened, and the valves in the drawings are indicated with outlines in the case where the valves are closed.

As shown in FIG. 7, the on-off valve 7*c*, the on-off valve V3, the on-off valve V5, and the on-off valve V2 are opened in the rehydration based blood return process (the normal direction in delivering liquid). Meanwhile, the air pump 7*a* rotates forward. Moreover, the blood pump 5 rotates forward. The opening of these on-off valves, the rotation of the air pump 7*a*, and the rotation of the blood pump 5 are controlled by instructions of the controller 12. In particular, the controller 12 controls the number of rotations of the air pump 7*a* per unit time (controls the flow rate of the air from the primary air introducer 7) in such a way as to generate the flow of the dialysate to the dialysate circuit 3 (the dialysate introduction circuit 3*a*), the rehydration circuit 4, and the blood circuit 2.

By driving the air pump 7*a* and opening the on-off valve 7*c*, the air is introduced into the dialysate filter 10 and the primary chamber 10*a* of the dialysate filter 10 is set to the positive pressure. Accordingly, the dialysate in the primary chamber 10*a* reaches the secondary chamber 10*b* and flows in the dialysate introduction circuit 3*a*. In other words, the controller 12 controls the dialysate circuit 3, the rehydration circuit 4, and the blood circuit 2 such that the dialysate flows in the flow route shown in FIG. 7.

By opening the on-off valve V3, the on-off valve V5, and the on-off valve V2, the dialysate passes through the dialysate introduction circuit 3*a*, the blood removal side rehydration circuit 4*a*, the blood removal side circuit 2*a*, the blood purifier 1 (the blood flow route), and the blood return side circuit 2*b*. In FIG. 7, this flow of the dialysate is indicated with an arrow of a thick chain line. By this flow of the dialysate, the dialysate pushes out the blood remaining in the blood purifier 1 and the blood circuit 2 (the blood return side circuit 2*b*), and the blood is returned to the body.

The rehydration based blood return process (the normal direction in delivering liquid) described with reference to FIG. 7 is carried out by operating at least the controller 12, the on-off valve 7*c*, the on-off valve V3, the on-off valve V5, the on-off valve V2, the air pump 7*a*, and the blood pump 5 only by the power supply from the backup power source 13. On the other hand, the constituents such as the dual pump 9 for feeding the dialysate to the dialysate circuit 3 and feeding the blood to the blood circuit 2 in the dialysis treatment may be stopped.

In the case where the dialysate in the dialysate filter 10 flows, the supply source of the dialysate is switched from the dialysate filter 10 to the dialysate filter 11. The switching of the supply source of the dialysate has been described in the first embodiment, and detailed explanations thereof will be omitted. In the case where the supply source of the dialysate is switched from the dialysate filter 10 to the dialysate filter 11, the rehydration based blood return process (the normal direction in delivering liquid) is carried out by using the dialysate in the dialysate filter 11.

As described above, in the second embodiment, the rehydration based blood return process (the normal direction in delivering liquid) is carried out by using the dialysate in the dialysate filter 10. In the configuration according to the second embodiment, no pressure is generated in the blood circuit 2 for drawing out the dialysate, and the blood circuit 2 is hence not set to the negative pressure either. The same applies to the case of using the dialysate in the dialysate filter 11. Therefore, according to the configuration of the second embodiment, it is possible to carry out the blood return more favorably as compared to the related art even in the case where the dialysate supplier 6 stops the generation and the supply of the dialysate.

Moreover, only the controller 12, the on-off valve 7*c*, the on-off valve V3, the on-off valve V5, the on-off valve V2, the air pump 7*a*, and the blood pump 5 are operated in the configuration according to the second embodiment. From this perspective, it is possible to carry out the blood return by the power supply from the backup power source 13 to the minimum required constituents particularly in the case where the power supply from the main power source to the blood purification apparatus 200 is stopped.

Note that the dialysate passes through the blood pump 5 in the rehydration based blood return process (the normal direction in delivering liquid), and the blood pump 5 therefore has to be driven. Accordingly, the pressure for drawing out the dialysate is generated in the blood circuit 2. In order not to set the blood circuit 2 to the negative pressure, the air pump 7*a* (or the air pump 8*a*) and/or the blood pump 5 are controlled such that the pressure in the dialysate circuit 3 caused by the introduction of the air into the dialysate filter 10 (or the dialysate filter 11) does not exceed a predetermined threshold (or becomes higher than the pressure in the blood circuit 2 generated by driving the blood pump 5). This control has been described in the first embodiment and detailed explanations thereof will be omitted.

In the rehydration based blood return process, a rehydration based blood return process (the reverse direction in delivering liquid) to return the blood to the body in the reverse direction in delivering liquid may be carried out instead of or in addition to the blood return process described with reference to FIG. 7. FIG. 8 shows a flow of the dialysate in the case of carrying out the rehydration based blood return process (the reverse direction in delivering liquid) by using the dialysate in the dialysate filter 10.

Figure 8:
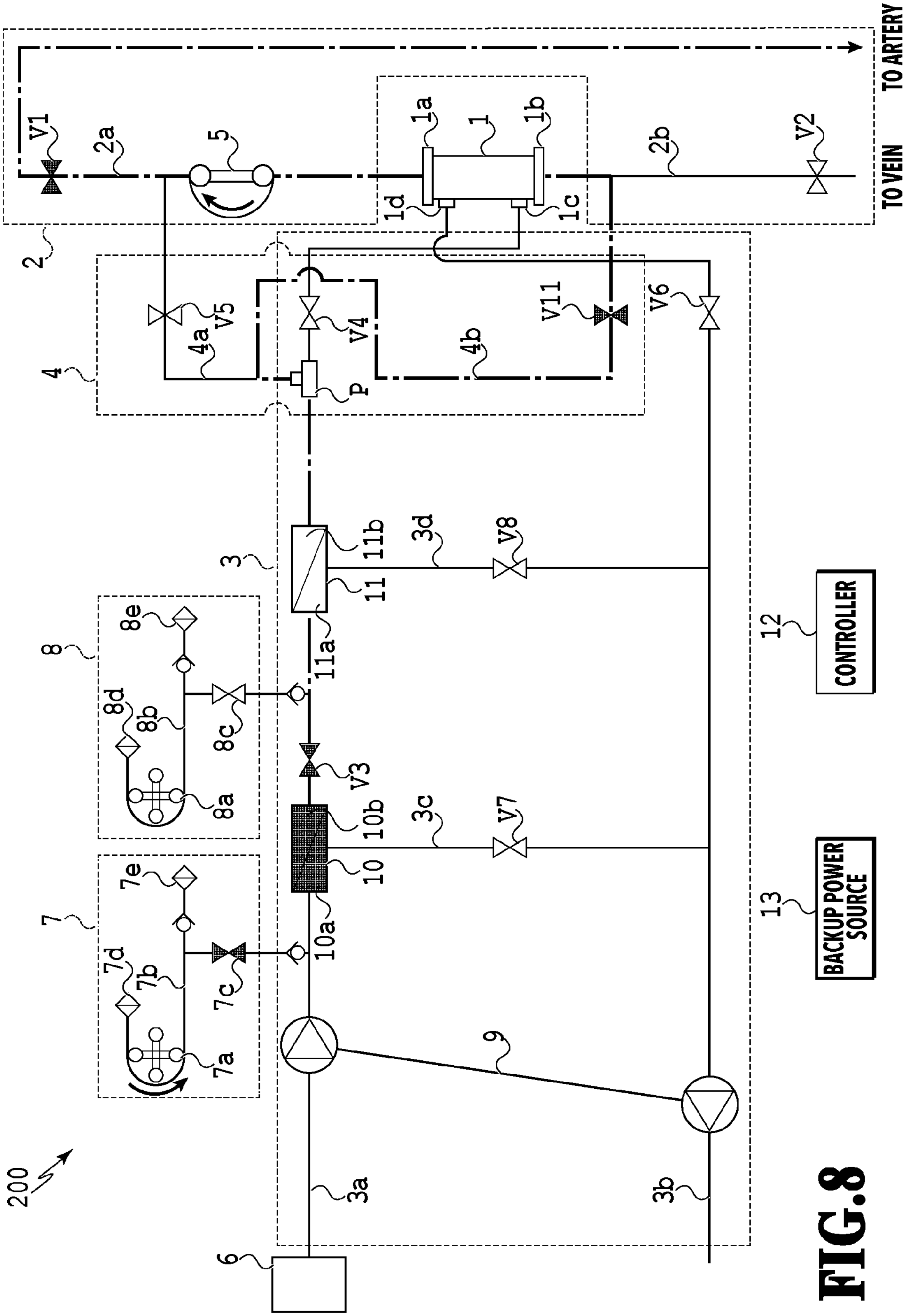
FIG. 8 is a diagram showing a flow of the dialysate in the rehydration based blood return process (the reverse direction in delivering liquid) by using the dialysate in the (primary) dialysate filter.

As shown in FIG. 8, the on-off valve 7*c*, the on-off valve V3, the on-off valve V11, and the on-off valve V1 are opened in the rehydration based blood return process (the reverse direction in delivering liquid). Meanwhile, the air pump 7*a* rotates forward. Moreover, the blood pump 5 rotates in reverse. The opening of these on-off valves, the rotation of the air pump 7*a*, and the rotation of the blood pump 5 are controlled by instructions of the controller 12. In particular, the controller 12 controls the number of rotations of the air pump 7*a* per unit time (controls the flow rate of the air from the primary air introducer 7) in such a way as to generate the flow of the dialysate to the dialysate circuit 3 (the dialysate introduction circuit 3*a*), the rehydration circuit 4, and the blood circuit 2.

By driving the air pump 7*a* and opening the on-off valve 7*c*, the air is introduced into the dialysate filter 10 and the primary chamber 10*a* of the dialysate filter 10 is set to the positive pressure. Accordingly, the dialysate in the primary chamber 10*a* reaches the secondary chamber 10*b* and flows in the dialysate introduction circuit 3*a*. In other words, the controller 12 controls the dialysate circuit 3, the rehydration circuit 4, and the blood circuit 2 such that the dialysate flows in the flow route shown in FIG. 8.

By opening the on-off valve V3, the on-off valve V11, and the on-off valve V1, the dialysate passes through the dialysate introduction circuit 3*a*, the blood return side rehydration circuit 4*b*, the blood return side circuit 2*b*, the blood purifier 1 (the blood flow route), and the blood removal side circuit 2*a*. In FIG. 8, this flow of the dialysate is indicated with an arrow of a thick chain line. By this flow of the dialysate, the dialysate pushes out the blood remaining in the blood purifier 1 and the blood circuit 2 (the blood removal side circuit 2*a*), and the blood is returned to the body.

The rehydration based blood return process (the reverse direction in delivering liquid) described with reference to FIG. 8 is carried out by operating at least the controller 12, the on-off valve 7*c*, the on-off valve V3, the on-off valve V7, the on-off valve V1, the air pump 7*a*, and the blood pump 5 only by the power supply from the backup power source 13. On the other hand, the constituents such as the dual pump 9 for feeding the dialysate to the dialysate circuit 3 in the dialysis treatment may be stopped.

In the case where the dialysate in the dialysate filter 10 flows, the supply source of the dialysate is switched from the dialysate filter 10 to the dialysate filter 11. The switching of the supply source of the dialysate has been described in the first embodiment, and detailed explanations thereof will be omitted. In the case where the supply source of the dialysate is switched from the dialysate filter 10 to the dialysate filter 11, the rehydration based blood return process (the reverse direction in delivering liquid) is carried out by using the dialysate in the dialysate filter 11.

The blood pump 5 has to be driven since the dialysate passes through the blood pump 5 in the rehydration based blood return process (the reverse direction in delivering liquid). Accordingly, the pressure for drawing out the dialysate is generated in the blood circuit 2. In order not to set the blood circuit 2 to the negative pressure, the air pump 7*a* (or the air pump 8*a*) and/or the blood pump 5 are controlled such that the pressure in the dialysate circuit 3 does not exceed a predetermined threshold (or becomes higher than the pressure in the blood circuit 2). This control has been described in the first embodiment and detailed explanations thereof will be omitted.

Here, both of the rehydration based blood return process (the normal direction in delivering liquid) and the rehydration based blood return process (the reverse direction in delivering liquid) may be carried out. For example, the rehydration based blood return process (the normal direction in delivering liquid) may be carried out in the first place by using the dialysate in the dialysate filter 10, and the rehydration based blood return process (the reverse direction in delivering liquid) may be carried out by using the dialysate in the dialysate filter 11 in the case of switching the supply source of the dialysate. Alternatively, the rehydration based blood return process (the reverse direction in delivering liquid) may be carried out in the first place by using the dialysate in the dialysate filter 10, and the rehydration based blood return process (the normal direction in delivering liquid) may be carried out by using the dialysate in the dialysate filter 11 in the case of switching the supply source of the dialysate. By carrying out both of the rehydration based blood return process (the normal direction in delivering liquid) and the rehydration based blood return process (the reverse direction in delivering liquid), it is possible to return the blood remaining in both of the blood removal side circuit 2*a* and the blood return side circuit 2*b* to the body.

Third Embodiment

Figure 9:
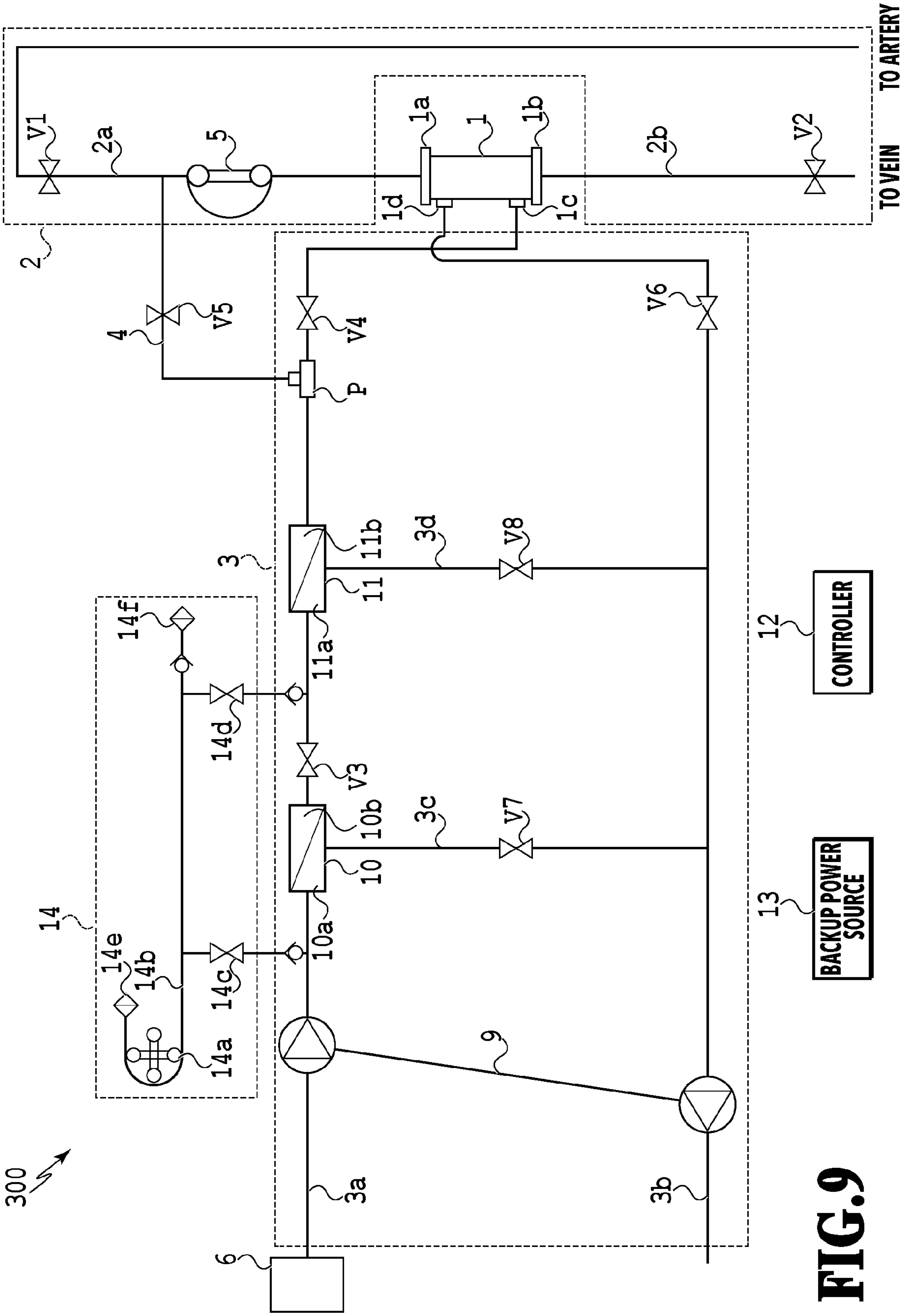
FIG. 9 is an overall configuration diagram of a blood purification apparatus according to a third embodiment.

FIG. 9 is a block diagram showing a configuration of a blood purification apparatus 300 according to a third embodiment. As compared to the blood purification apparatus 100 according to the first embodiment, the blood purification apparatus 300 has a different configuration of the air introducer (the primary air introducer 7 and the secondary air introducer 8) and the configurations of the rest are the same. The blood purification apparatus 300 includes an air introducer 14 instead of the primary air introducer 7 and the secondary air introducer 8.

The air introducer 14 plays the same role as the primary air introducer 7 and the secondary air introducer 8, and introduces the air into the dialysate filter 10 and the dialysate filter 11. The air introducer 14 includes an air pump 14*a*, an air introduction route 14*b*, an on-off valve (a solenoid valve) 14*c*, an on-off valve (a solenoid valve) 14*d*, an air filter 14*e*, and an air filter 14*f*. The air pump 14*a* incorporates a rotor and drives the rotor so as to perform rotation. The rotor is rotated by an actuator (not shown) such as an electric motor under control of the controller 12. The air pump 14*a* is provided with a rotary encoder (not shown). The rotary encoder detects the number of rotations of the rotor. By the rotation of the air pump 14*a*, the air is introduced into the dialysate filter 10 and the dialysate filter 11 through the air introduction route 14*b*.

Although not illustrated, the air introducer 14 is coupled to the blood removal side air trap chamber 2*c* and the blood return side air trap chamber 2*d* as with the primary air introducer 7 and the secondary air introducer 8 shown in FIG. 2. The air pump 14*a* also plays a role as a liquid level adjustment pump to adjust liquid levels in the blood removal side air trap chamber 2*c* and the blood return side air trap chamber 2*d* at the time of the dialysis treatment, for example.

The air introduced into the dialysate filter 10 and the dialysate filter 11 by the drive of the air pump 14*a* generates a flow of the dialysate to the dialysate circuit 3 (the dialysate introduction circuit 3*a*) and the blood circuit 2. The flow of the air to the dialysate filter 10 is controlled by opening and closing the on-off valve 14*c* provided between the air pump 14*a* and the dialysate filter 10. Likewise, the flow of the air to the dialysate filter 11 is controlled by opening and closing the on-off valve 14*d* provided between the air pump 14*a* and the dialysate filter 11. The air filter 14*e* and the air filter 14*f* remove dust in the air. The air filter 14*e* and the air filter 14*f* are not essential structures in the air introducer 14.

As compared to the first embodiment and the second embodiment, the third embodiment only provides the air pump 14*a* (e.g., a single pump that is common to a first air introduction route and a second air introduction route) instead of providing the pair of the air pump 7*a* and the air pump 8*a*. Similarly, the third embodiment only provides the air introduction route 14*b* instead of providing the pair of the air introduction route 7*b* and the air introduction route 8*b*. In this way, the configuration of the entire device is further simplified.

Next, processing according to the third embodiment will be described with reference to FIGS. 10 and 11. In the third embodiment, a description will be given only of an example of returning the blood remaining in the blood purifier 1 and the blood circuit 2 to the body the back filtration based blood return process (the normal direction in delivering liquid) while using the dialysate in the dialysate filter 10 and the dialysate filter 11. However, the blood return in accordance with any of the back filtration based blood return process (the reverse direction in delivering liquid), the rehydration based blood return process (the normal direction in delivering liquid), and the rehydration based blood return process (the reverse direction in delivering liquid) may also be carried in the third embodiment as well. Only some of the constituents in the blood purification apparatus 300 to be described later function by the power supply from the backup power source 13 in the third embodiment as well.

Figure 10:
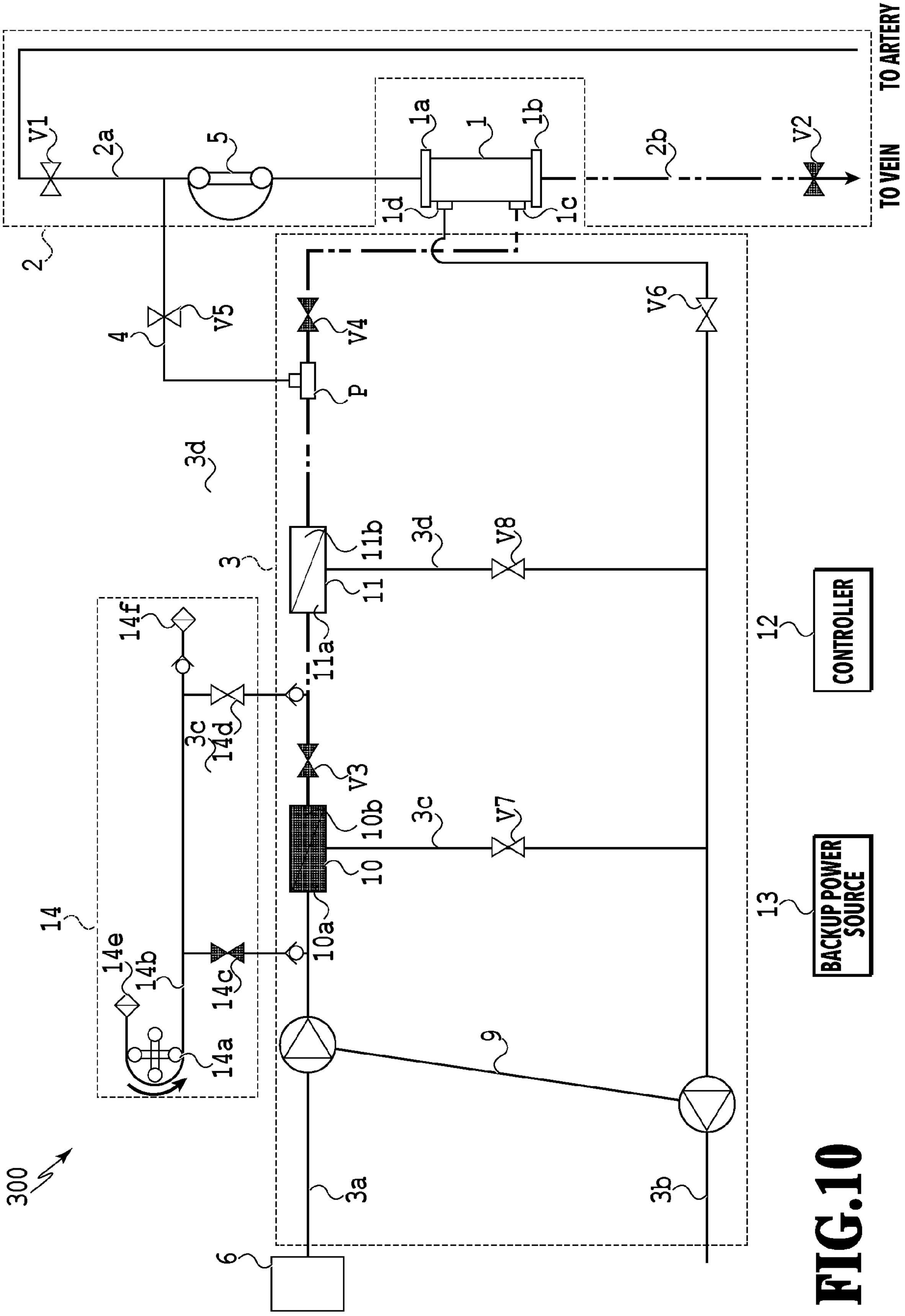
FIG. 10 is a diagram showing a flow of the dialysate in the back filtration based blood return process (the normal direction in delivering liquid) by using the dialysate in the (primary) dialysate filter.

FIG. 10 shows a flow of the dialysate in the case where the back filtration based blood return process (the normal direction in delivering liquid) is carried out by using the dialysate in the dialysate filter 10. In the following drawings, valves among the valves in the drawings are indicated with hatching in the case where the valves are opened, and the valves in the drawings are indicated with outlines in the case where the valves are closed.

As shown in FIG. 10, the on-off valve 14*c*, the on-off valve V3, the on-off valve V4, and the on-off valve V2 are opened in the back filtration based blood return process (the normal direction in delivering liquid). Meanwhile, the air pump 14*a* rotates forward. The opening of these on-off valves and the rotation of the air pump 14*a* are controlled by instructions of the controller 12. In particular, the controller 12 controls the number of rotations of the air pump 14*a* per unit time (controls the flow rate of the air from the air introducer 14) in such a way as to generate the flow of the dialysate to the dialysate circuit 3 (the dialysate introduction circuit 3*a*) and the blood circuit 2.

By driving the air pump 14*a* and opening the on-off valve 14*c*, the air is introduced into the dialysate filter 10 and the primary chamber 10*a* of the dialysate filter 10 is set to the positive pressure. Accordingly, the dialysate in the primary chamber 10*a* reaches the secondary chamber 10*b* and flows in the dialysate introduction circuit 3*a*. In other words, the controller 12 controls the dialysate circuit 3 and the blood circuit 2 such that the dialysate flows in the flow route shown in FIG. 10.

By opening the on-off valve V3, the on-off valve V4, and the on-off valve V2, the dialysate passes through the dialysate introduction circuit 3*a*, the blood purifier 1 (the blood purification membrane), and the blood return side circuit 2*b*. In FIG. 10, this flow of the dialysate is indicated with an arrow of a thick chain line. Here, the dialysate flows inside the blood purifier 1 in the order of the dialysate flow route, the blood purification membrane, and the blood flow route. By this flow of the dialysate, the dialysate pushes out the blood remaining in the blood purifier 1 and the blood circuit 2 (the blood return side circuit 2*b*), and the blood is returned to the body.

The back filtration based blood return process (the normal direction in delivering liquid) described with reference to FIG. 10 is carried out by operating at least the controller 12, the on-off valve 14*c*, the on-off valve V3, the on-off valve V4, the on-off valve V2, and the air pump 14*a* only by the power supply from the backup power source 13. On the other hand, the constituents such as the blood pump 5 and the dual pump 9 for feeding the dialysate to the dialysate circuit 3 and feeding the blood to the blood circuit 2 in the dialysis treatment may be stopped.

In the case where the dialysate in the dialysate filter 10 flows, the supply source of the dialysate is switched from the dialysate filter 10 to the dialysate filter 11. The switching of the supply source of the dialysate has been described in the first embodiment, and detailed explanations thereof will be omitted. FIG. 11 shows a flow of the dialysate in the case where the back filtration based blood return process (the normal direction in delivering liquid) is carried out by using the dialysate in the dialysate filter 11.

Figure 11:
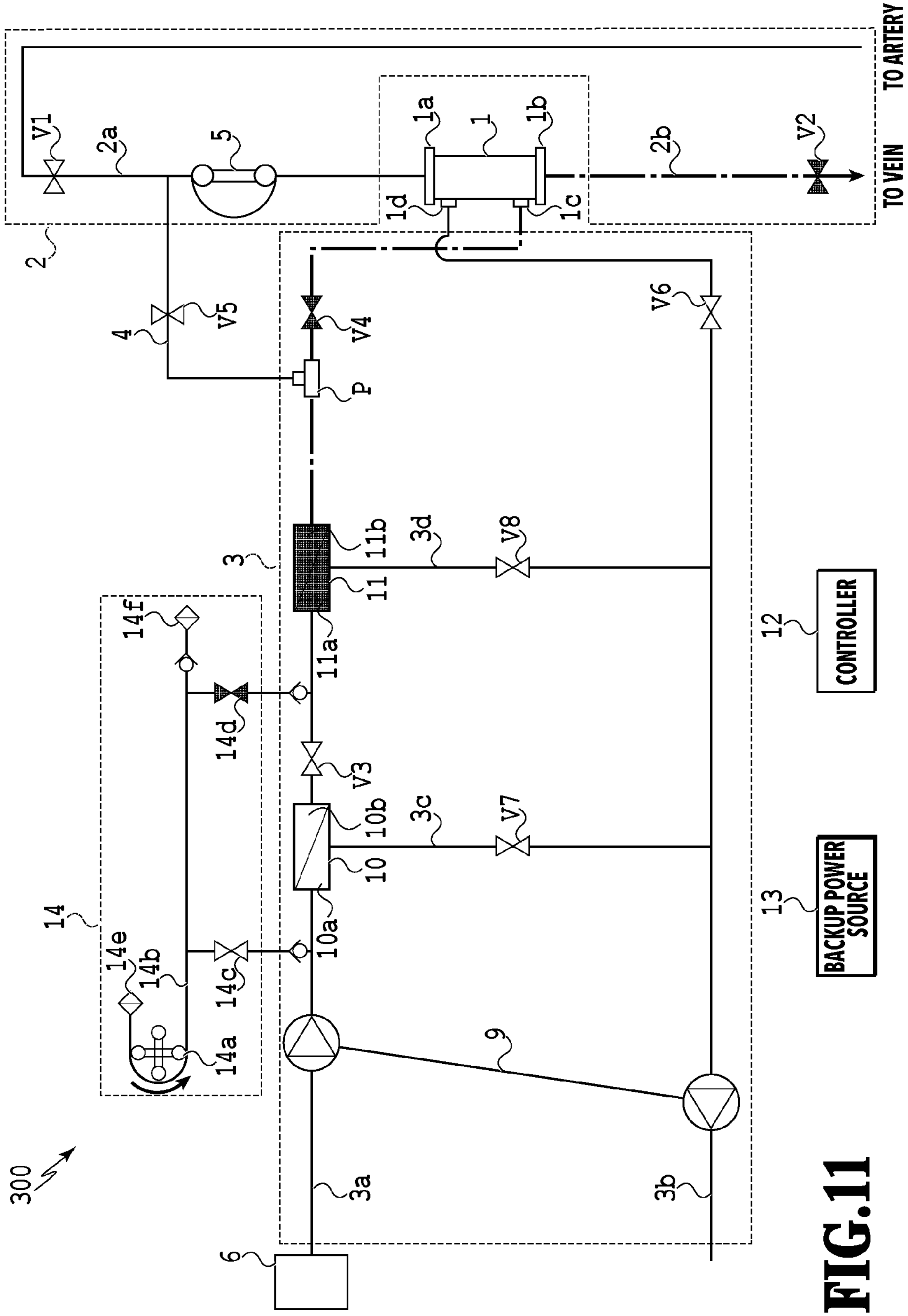
FIG. 11 is a diagram showing a flow of the dialysate in the back filtration based blood return process (the normal direction in delivering liquid) by using the dialysate in the (primary) dialysate filter.

As shown in FIG. 11, the on-off valve 14*c* is closed in the case where the supply source of the dialysate is switched from the dialysate filter 10 to the dialysate filter 11. Meanwhile, the on-off valve 14*d* is opened. The opening and closing of these on-off valves are controlled by instructions of the controller 12. In particular, the controller 12 controls the number of rotations of the air pump 14*a* per unit time (controls the flow rate of the air from the air introducer 14) in such a way as to generate the flow of the dialysate to the dialysate circuit 3 (the dialysate introduction circuit 3*a*) and the blood circuit 2.

By driving the air pump 14*a* and opening the on-off valve 14*d*, the air is introduced into the dialysate filter 11 and the primary chamber 11*a* of the dialysate filter 11 is set to the positive pressure. Accordingly, the dialysate in the primary chamber 11*a* reaches the secondary chamber 11*b* and flows in the dialysate introduction circuit 3*a*. Thereafter, the dialysate flows in the same flow route as the flow route shown in FIG. 11. In other words, the controller 12 controls the dialysate circuit 3 and the blood circuit 2 such that the dialysate flows in the flow route shown in FIG. 11. In FIG. 11, this flow of the dialysate is indicated with an arrow of a thick chain line.

The back filtration based blood return process (the normal direction in delivering liquid) described with reference to FIG. 11 is carried out by operating at least the controller 12, the on-off valve 14*d*, the on-off valve V3, the on-off valve V4, the on-off valve V2, and the air pump 14*a* only by the power supply from the backup power source 13. On the other hand, the blood pump 5, the dual pump 9, and the like may be stopped.

As described above, in the third embodiment, the supply source of the dialysate is switched by using the single air introducer 14. The configuration according to the third embodiment does not have to drive the blood pump 5 either. Moreover, in the configuration according to the third embodiment, no pressure is generated in the blood circuit 2 for drawing out the dialysate, and the blood circuit 2 is hence not set to the negative pressure either. Therefore, according to the configuration of the third embodiment, it is possible to carry out the blood return more favorably as compared to the related art even in the case where the dialysate supplier 6 stops the generation and the supply of the dialysate.

Although the above-described first to third embodiments use the two dialysate filters (the dialysate filter 10 and the dialysate filter 11), a single dialysate filter or three or more dialysate filters may be used instead. In other words, the blood remaining in the blood purifier 1 and the blood circuit 2 is returned to the body by using the dialysate in n pieces (n is an integer equal to or larger than 1) of dialysate filters. In the case of using three or more dialysate filters, for example, the supply source of the dialysate is switched in three steps in accordance with the above-described determination method. While the blood return is carried out by using the dialysate stored in the dialysate filter 10 and the dialysate filter 11, a dedicated chamber for storing the dialysate may be provided instead.

Meanwhile, in the first to third embodiments, the primary air introducer 7 may be configured to include a compressed air tank encapsulating compressed air instead of including the air pump 7*a*. In the case of this configuration, the air is introduced from the compressed air tank to the dialysate filter 10 through the air introduction route 7*b* by opening the on-off valve 7*c*. Likewise, the secondary air introducer 8 and the air introducer 14 may also be configured to include compressed air tanks instead of including the air pump 8*a* and the air pump 14*a*. In addition thereto, the rotations of the air pump 7*a*, the air pump 8*a*, the air pump 14*a*, and the blood pump 5 are controlled by using the rotary encoders. Here, the rotations may be controlled by using other modes instead. For example, the rotations of the air pump 7*a*, the air pump 8*a*, the air pump 14*a*, and the blood pump 5 may be carried out based on open loop control using a pulse motor.

In addition, the back filtration based blood return processes (the normal direction in delivering liquid and the reverse direction in delivering liquid) and the rehydration based blood return processes (the normal direction in delivering liquid and the reverse direction in delivering liquid) may be combined as desired. For example, the rehydration based blood return process (the normal direction in delivering liquid) may be carried out in the first place by using the dialysate in the dialysate filter 10, and the back filtration based blood return process (the reverse direction in delivering liquid) may be carried out by using the dialysate in the dialysate filter 11 in the case of switching the supply source of the dialysate.

In addition, the above-described first to third embodiments are mainly applied to the blood return processes. However, the present disclosure is not limited only to these examples. The above-described processing may also be applied to a fluid replacement process for preventing a blood pressure drop caused by reduction in blood of the patient due to a water removal process to remove extra water from the blood, and the like. In the fluid replacement process, the dialysate is injected to the blood circuit so as to supplement the blood in the body.

The above-described embodiments are mere examples. The scope of the embodiments is not limited only to the described examples. Extra processing and/or constituents may be added to the above-described processing and constituents. Meanwhile, the above-described processing and/or constituents may be subjected to modifications without departing from the scope of the invention. Alternatively, a specific part of the above-described processing and/or constituents may be omitted. Moreover, the described order of processing may be changed.

The blood purification apparatus according to the embodiments is implemented by a computer program to be executed by the controller 12. Here, the computer program may be stored in a non-transitory storage medium. Examples of the non-transitory storage medium include a read only memory (ROM), a random access memory (RAM), a register, a cache memory, a semiconductor memory device, a magnetic medium such as a built-in hard disk drive and a removable disk drive, a magneto-optical medium, an optical medium such as a CD-ROM disc and a digital versatile disc (DVD), and so forth.

REFERENCE SIGNS LIST

1 blood purifier
1*a* blood introduction inlet
1*b* blood introduction outlet
1*c* dialysate introduction inlet
1*d* dialysate drainage outlet
2 blood circuit
2*a* blood removal side circuit
2*b* blood return side circuit
2*c* blood removal side air trap chamber
2*d* blood return side air trap chamber
3 dialysate circuit
3*a* dialysate introduction circuit
3*b* dialysate drainage circuit
4 rehydration circuit
4*a* blood removal side rehydration circuit
4*b* blood return side rehydration circuit
5 blood pump
6 dialysate supplier
7 primary air introducer
7*a* air pump
7*b* air introduction route
7*c* on-off valve
7*d* air filter
7*e* air filter
8 secondary air introducer
8*a* air pump
8*b* air introduction route
8*c* on-off valve
8*d* air filter
8*e* air filter
9 dual pump
10 dialysate filter
10*a* primary chamber
10*b* secondary chamber
11 dialysate filter
11*a* primary chamber
11*b* secondary chamber
12 controller
13 backup power source
14 air introducer
14*a* air pump
14*b* air introduction route
14*c* on-off valve
14*d* on-off valve
14*e* air filter
14*f* air filter
100 blood purification apparatus
200 blood purification apparatus
300 blood purification apparatus
P dialysate port
V1 to V11 on-off valve

The invention claimed is:

1. A blood purification apparatus comprising:

a blood circuit and a dialysate circuit coupled to each other through a blood purifier;

a chamber provided to the blood circuit and configured to store the blood in the blood circuit;

an air introduction route coupled to the dialysate circuit;

an air introducer provided to any of the dialysate circuit and the air introduction route and configured to set the dialysate circuit to a positive pressure by introducing air into the dialysate circuit through the air introduction route, wherein the air introducer is coupled to the chamber and configured to adjust a liquid level in the chamber by feeding the air into the chamber; and a controller configured to control the air introducer in such a way as to feed a dialysate from the dialysate circuit to the blood circuit, and to control the blood circuit and the dialysate circuit in such a way as to return blood in the blood circuit and the blood purifier to a body by feeding the dialysate from the dialysate circuit to the blood circuit, wherein the controller controls the air introducer in such a way as to introduce the air into the dialysate circuit without feeding the air into the chamber in a case of returning the blood in the blood circuit and the blood purifier to the body.

2. The blood purification apparatus according to claim 1, further comprising:

a dialysate filter provided to the dialysate circuit and configured to purify and store the dialysate flowing in the dialysate circuit, wherein the air introducer introduces the air into the dialysate filter and pushes the dialysate stored in the dialysate filter out to the dialysate circuit.

3. The blood purification apparatus according to claim 2, wherein the dialysate filter includes at least a first dialysate filter and a second dialysate filter, and the controller controls the air introducer in such a way as to introduce the air into the second dialysate filter in a case where the controller determines that the dialysate stored in the first dialysate filter is pushed out to the dialysate circuit.

4. The blood purification apparatus according to claim 3, further comprising:

a first on-off valve provided between the air introducer and the first dialysate filter; and a second on-off valve provided between the air introducer and the second dialysate filter, wherein the controller performs control in such a way as to close the first on-off valve and to open the second on-off valve in the case where the controller determines that the dialysate stored in the first dialysate filter is pushed out to the dialysate circuit.

5. The blood purification apparatus according to claim 1, wherein the controller controls the dialysate circuit and the blood circuit such that the dialysate flows from the dialysate circuit to the blood circuit through the blood purifier.

6. The blood purification apparatus according to claim 5, wherein the blood circuit includes a blood return side circuit, and the controller controls the dialysate circuit and the blood circuit such that the dialysate flows from the dialysate circuit to the blood return side circuit through the blood purifier.

7. The blood purification apparatus according to claim 5, wherein the blood circuit includes a blood removal side circuit, and the controller controls the dialysate circuit and the blood circuit such that the dialysate flows from the dialysate circuit to the blood removal side circuit through the blood purifier.

8. The blood purification apparatus according to claim 1, wherein the controller controls a flow rate of the air from the air introducer such that the dialysate flows from the dialysate circuit to the blood circuit.

9. The blood purification apparatus according to claim 8, wherein the controller controls the air introducer such that a pressure in the dialysate circuit generated by introducing the air into the dialysate circuit does not exceed a predetermined threshold.

10. The blood purification apparatus according to claim 1, further comprising:

a blood pump configured to be driven in such a way as to deliver a liquid in the blood circuit, wherein the controller controls the blood pump in such a way as not to drive the blood pump.

11. The blood purification apparatus according to claim 1, further comprising:

a blood pump configured to be driven in such a way as to deliver a liquid in the blood circuit, wherein at least one of the air introducer and the blood pump is controlled in such a way as to achieve a higher pressure than a pressure in the blood circuit generated by driving the blood pump.

12. The blood purification apparatus according to claim 1, wherein the air introduction route includes a first air introduction route coupled to the dialysate circuit, and a second air introduction route coupled to the dialysate circuit at a location different from the first air introduction route, the air introducer includes a single pump, and the single pump is used in common in a case where the air introducer introduces the air through the first air introduction route and in a case where the air introducer introduces the air through the second air introduction route.

13. A method to be executed by a blood purification apparatus provided with a blood circuit and a dialysate circuit coupled to each other through a blood purifier, a chamber provided to the blood circuit and configured to store the blood in the blood circuit, an air introduction route coupled to the dialysate circuit, an air introducer provided to any of the dialysate circuit and the air introduction route and configured to set the dialysate circuit to a positive pressure by introducing air into the dialysate circuit through the air introduction route, wherein the air introducer is coupled to the chamber and configured to adjust a liquid level in the chamber by feeding the air into the chamber, and a controller configured to control a pressure in the blood circuit and the dialysate circuit, wherein the blood circuit includes a blood removal side circuit which is a flow route for introducing blood into the blood purifier, and a blood return side circuit which discharges the blood from the blood purifier, the method comprising steps of:

causing the controller to control the air introducer in such a way as to feed a dialysate from the dialysate circuit to the blood return side circuit;

causing the controller to control the blood circuit and the dialysate circuit in such a way as to discharge blood in the blood removal side circuit and the blood purifier to a blood return side circuit by feeding the dialysate from the dialysate circuit to the blood return side circuit; and controlling, with the controller, the air introducer in such a way as to introduce the air into the dialysate circuit without feeding the air into the chamber in a case of discharging the blood in the blood removal side circuit and the blood purifier to the blood return side circuit.

* * * * *